US010201436B2

(12) United States Patent
Ikedo et al.

(10) Patent No.: US 10,201,436 B2
(45) Date of Patent: Feb. 12, 2019

(54) JOINT MECHANISM CONTROL DEVICE

(71) Applicant: HONDA MOTOR CO., LTD., Minato-Ku, Tokyo (JP)

(72) Inventors: Yosuke Ikedo, Saitama (JP); Toru Takenaka, Saitama (JP); Hiroshi Gomi, Saitama (JP); Yoshinao Sodeyama, Saitama (JP); Kenichi Katagiri, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 469 days.

(21) Appl. No.: 14/978,657

(22) Filed: Dec. 22, 2015

(65) Prior Publication Data

US 2016/0184111 A1    Jun. 30, 2016

(30) Foreign Application Priority Data

Dec. 26, 2014    (JP) .................... 2014-266596

(51) Int. Cl.
*A61H 3/00* (2006.01)
*A61F 2/68* (2006.01)
*A61H 1/02* (2006.01)

(52) U.S. Cl.
CPC ............. *A61F 2/68* (2013.01); *A61H 1/0255* (2013.01); *A61H 3/00* (2013.01); *A61H 2201/0103* (2013.01); *A61H 2201/1215* (2013.01); *A61H 2201/149* (2013.01); *A61H 2201/1463* (2013.01); *A61H 2201/164* (2013.01); *A61H 2201/165* (2013.01);
(Continued)

(58) Field of Classification Search
CPC ........... A61F 2/68; A61H 1/0255; A61H 3/00; A61H 2201/1463; A61H 2201/164; A61H 2201/149; A61H 2201/1676; A61H 2201/1215; A61H 2201/0103; A61H 2201/165; A61H 2201/1645; A61H 2201/1623
See application file for complete search history.

(56) References Cited

U.S. PATENT DOCUMENTS

2008/0289670 A1* 11/2008 Ashihara ............... B25J 9/0006
                                                              135/65
2009/0292369 A1* 11/2009 Kazerooni ............ B25J 9/0006
                                                              623/27
(Continued)

FOREIGN PATENT DOCUMENTS

JP    2012-100983 A    5/2012
JP    2014-508010 A    4/2014
WO    2012/125765 A2   9/2012

*Primary Examiner* — Quang D Thanh
(74) *Attorney, Agent, or Firm* — Carrier Blackman & Associates, P.C.; Joseph P. Carrier; Fulchand P. Shende

(57) ABSTRACT

A present invention provides a joint power control device. A joint interlock displacement part (52) of a power transmission movable mechanism (53), which is comprising of a moving pulley (51) and the like, is connected to a joint mechanism (5) disposed between a first member (2) and a second member (3). A flexible lengthy member (32), which is one of two flexible lengthy members (32, 32) extending from the power transmission movable mechanism (53), is connected to a control mechanism (54) that controls the movement of the flexible lengthy member (32). Further, an elastic structure (31) is engaged with the other flexible lengthy member (32).

18 Claims, 15 Drawing Sheets

(52) U.S. Cl.
CPC ............... *A61H 2201/1623* (2013.01); *A61H 2201/1645* (2013.01); *A61H 2201/1676* (2013.01)

(56) References Cited

U.S. PATENT DOCUMENTS

| | | | | |
|---|---|---|---|---|
| 2009/0312844 A1* | 12/2009 | Ikeuchi | ................. | A61H 3/008 623/40 |
| 2010/0152630 A1* | 6/2010 | Matsuoka | .............. | A61H 3/008 601/35 |
| 2015/0051527 A1* | 2/2015 | Potter | ................. | A61F 5/0125 602/16 |

\* cited by examiner

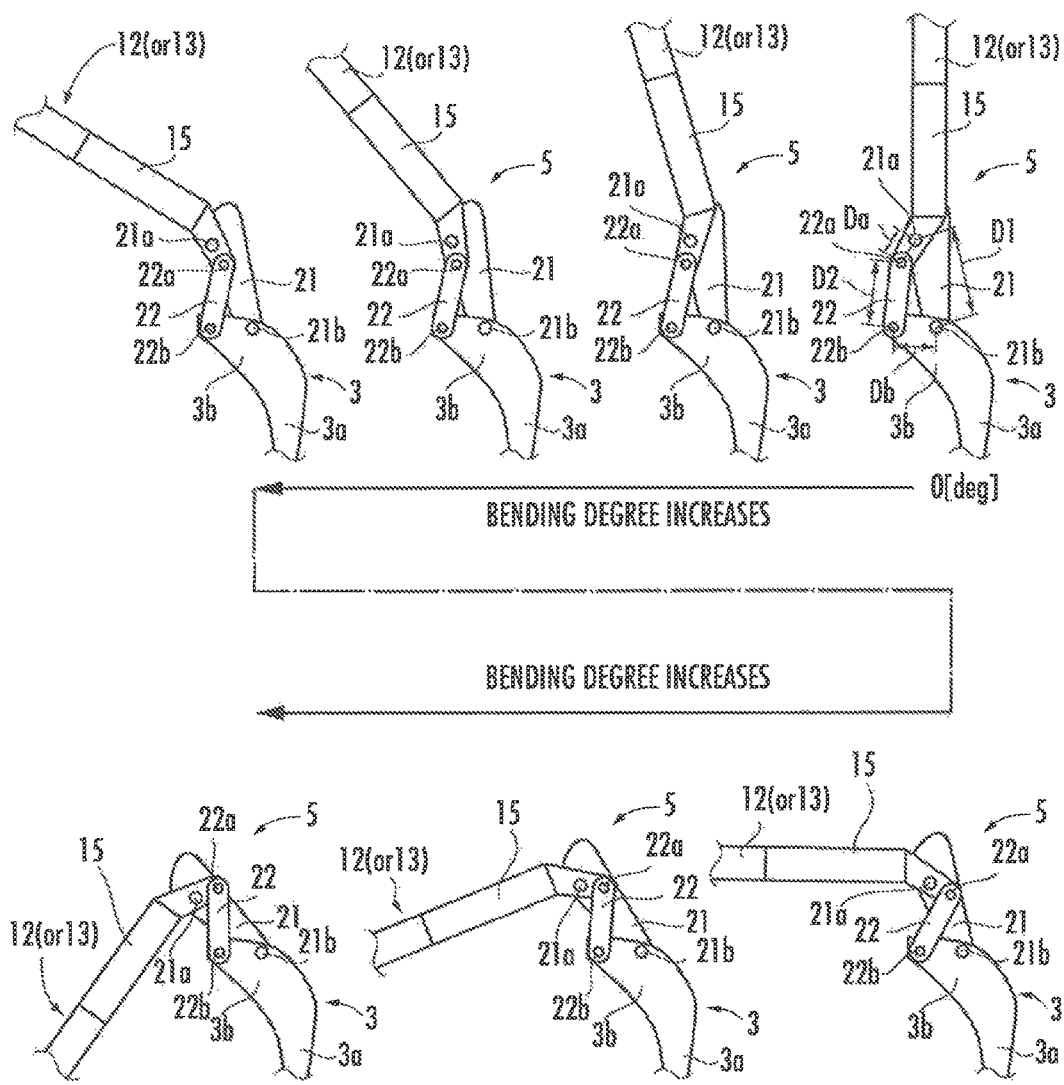

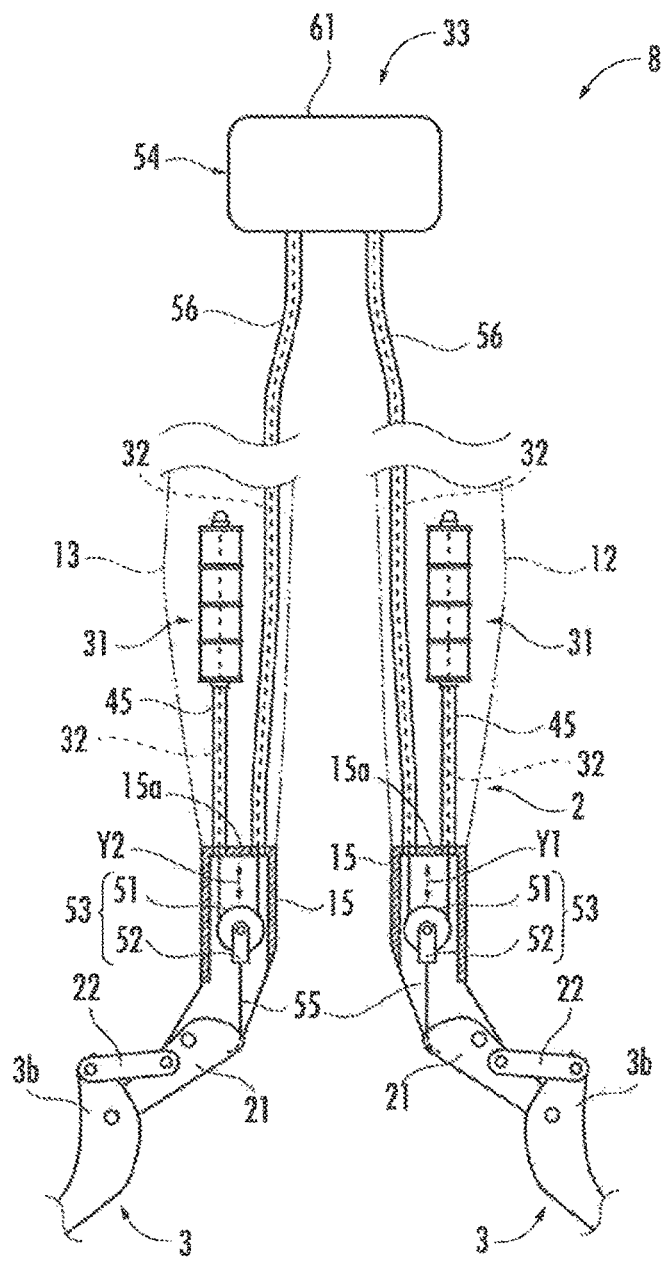

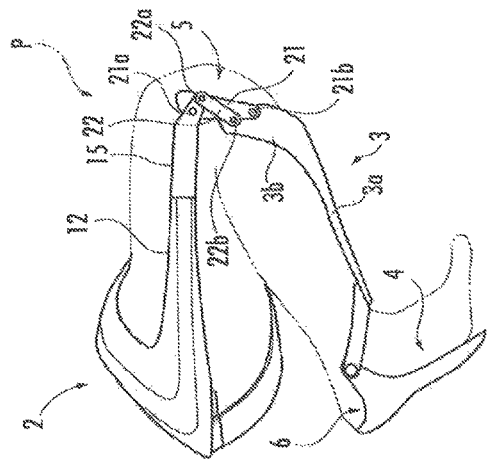
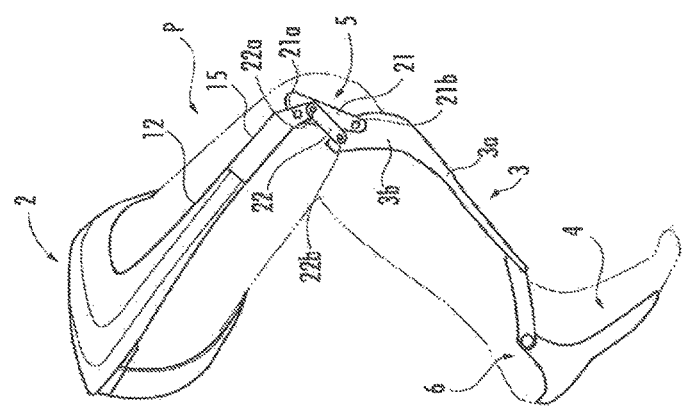
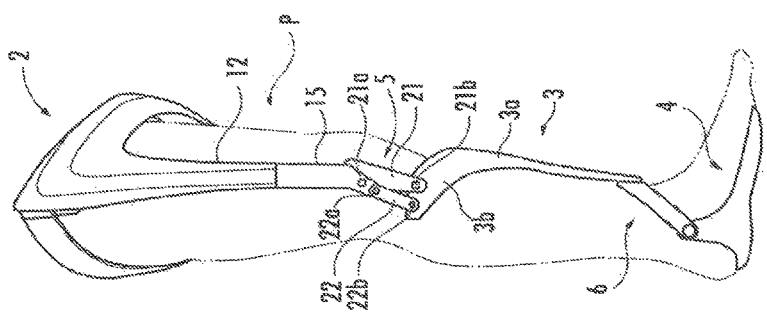

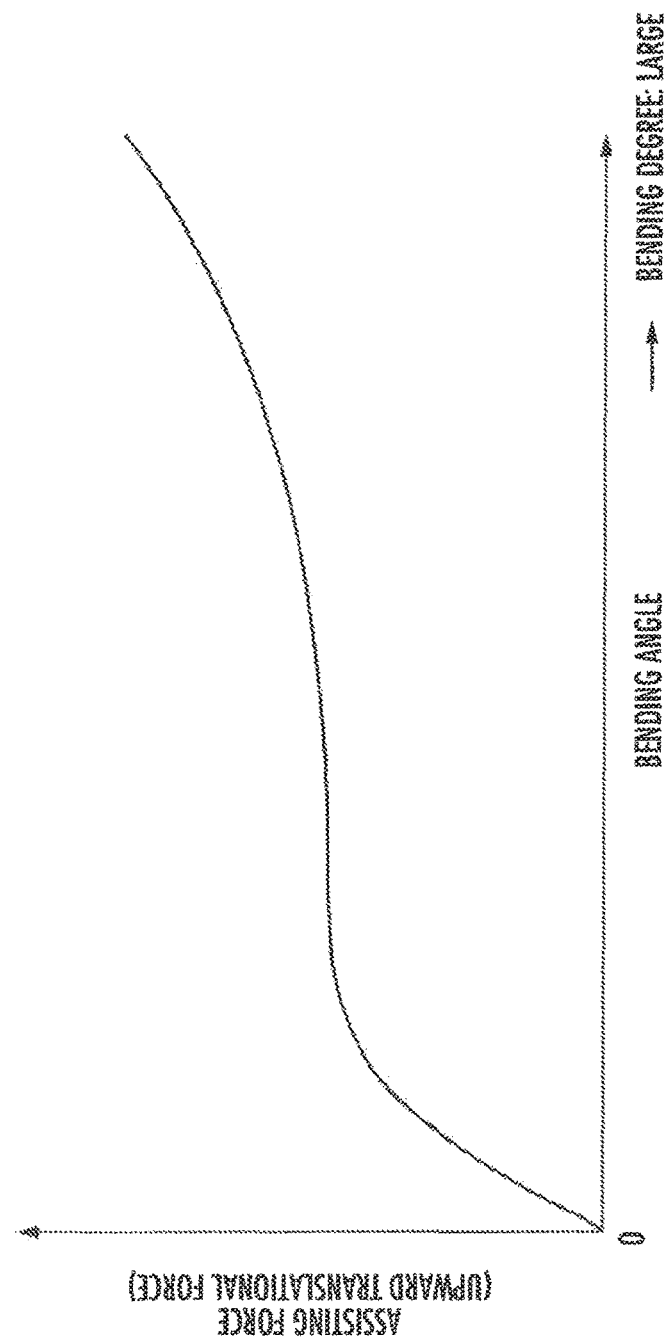

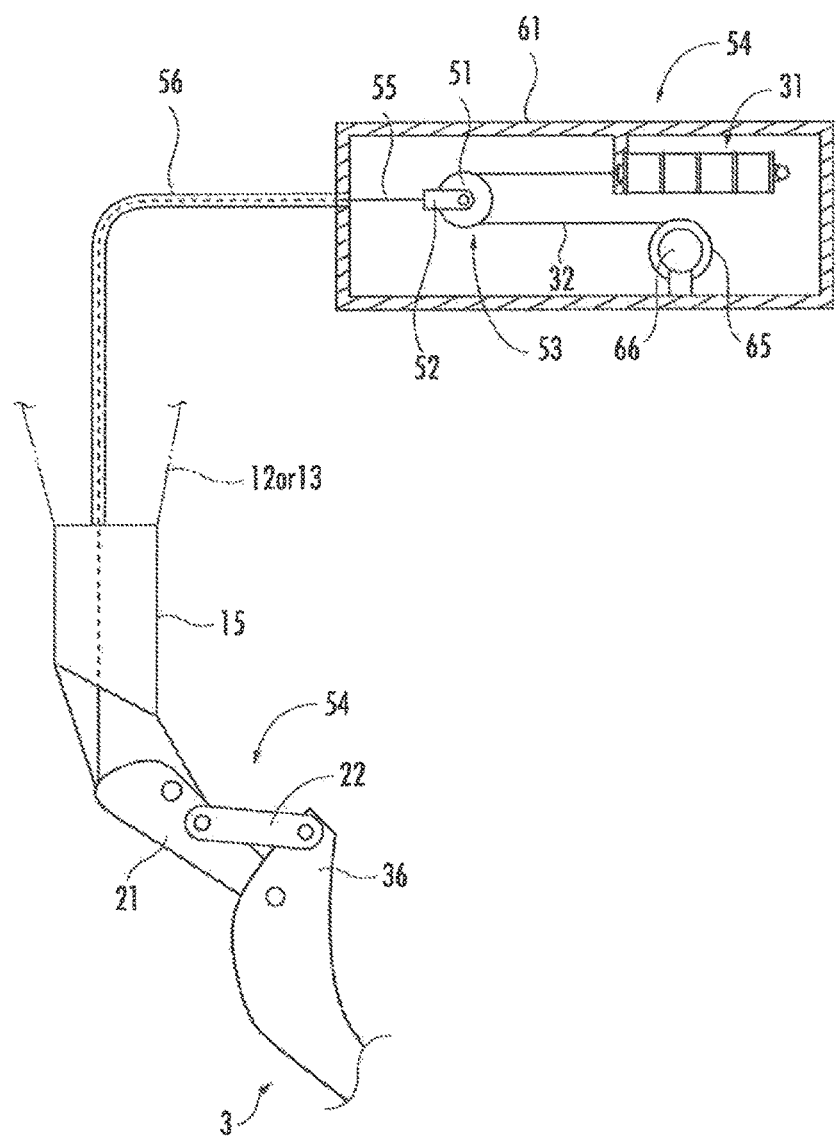

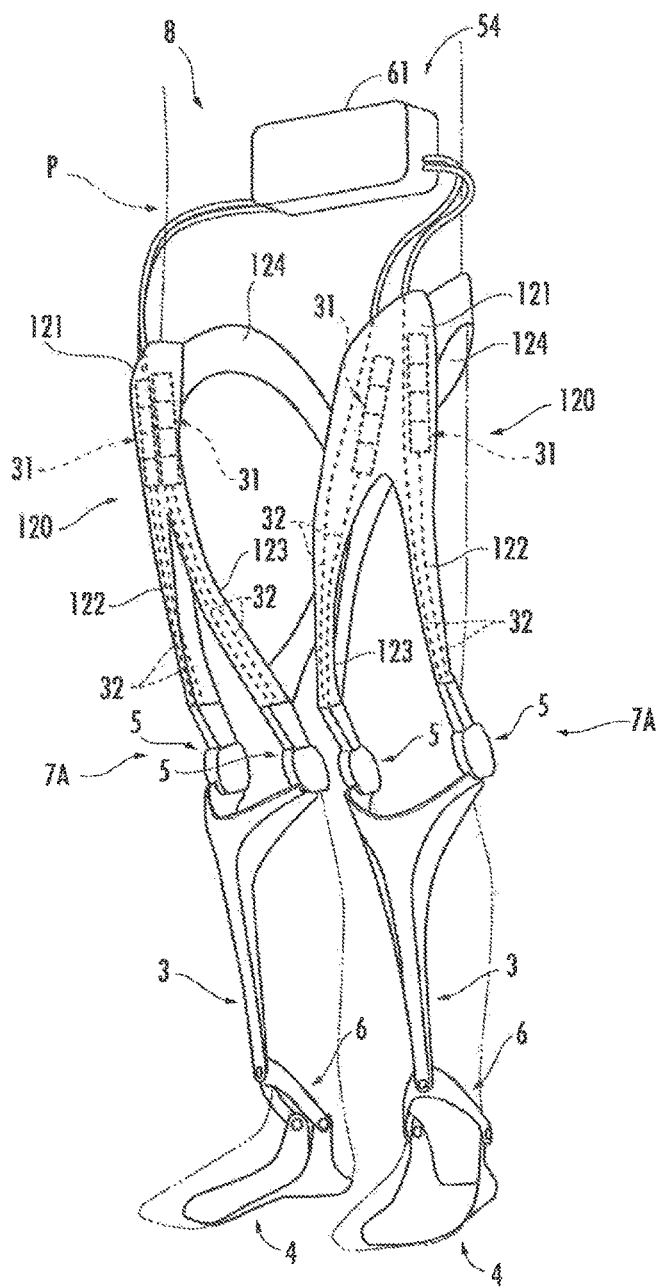

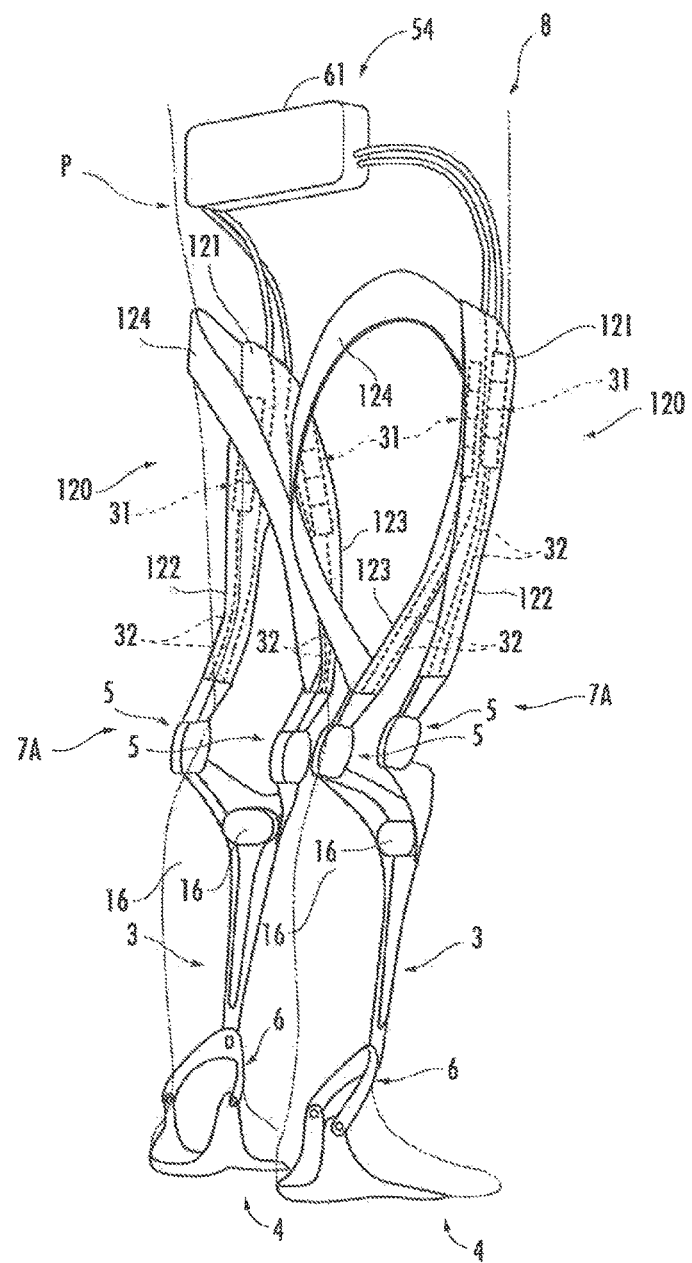

JOINT MECHANISM CONTROL DEVICE

FIELD OF THE INVENTION

The present invention relates to a joint power control device adapted to control the force, i.e. the joint power, to be imparted to a joint mechanism which connects two members in a relatively displaceable manner.

DESCRIPTION OF THE RELATED ART

As a device provided with a joint mechanism that connects two members in a relatively displaceable manner, there has hitherto been known, for example, a motion assisting apparatus adapted to be attached to the legs of a person to be assisted and to generate power for assisting the bending and stretching motions of the legs. For example, Japanese Patent Application Laid-Open No. 2014-508010 (hereinafter referred to as "Patent Document 1") discloses a motion assisting apparatus provided with thigh frames and crus frames to be attached to the thighs and the cruses, respectively, of the legs of a person to be assisted, and springs. The motion assisting apparatus uses the elastic forces of the springs to apply power to a joint mechanism between the thigh frame and the crus frame thereby to assist the motion of each leg.

In the conventional motion assisting apparatus as described in Patent Document 1, the power is imparted to the knee joint mechanism between the thigh frame and the crus frame only by the elastic force of the spring. Therefore, in order to impart relatively large power to the knee joint mechanism, the stiffness of the spring has to be increased. This inconveniently leads to an increased weight or size of the spring.

Further, in the motion assisting apparatus having the configuration described in Patent Document 1, the spring (coil spring) is displaced and contracted or expanded at a side of the thigh frame when the knee joint mechanism operates to perform the bending or stretching motion between the thigh frame and the crus frame. Hence, the space required for the operation of the spring tends to become larger.

Accordingly, the device for imparting the power to the knee joint mechanisms tends to become larger. In addition, the layout of the constituent elements of the device tends to be restricted.

SUMMARY OF THE INVENTION

The present invention has been made in view of the background described above, and an object of the invention is to provide a joint power control device which is capable of imparting sufficiently large power to a joint mechanism, which connects two members, by using an elastic structure, and which permits a reduction in a placement space or the like of the elastic structure.

To this end, a joint power control device in accordance with the present invention is a joint power control device that controls joint power which is a force to be imparted to a joint mechanism connecting a first member and a second member in a relatively displaceable manner, including: a power transmission movable mechanism having a joint interlock displacement part connected to the joint mechanism such that the joint interlock displacement part is displaced according to a change in an amount of relative displacement of the first member and the second member caused by a motion of the joint mechanism, and a first engagement part and a second engagement part, which are engaged with a first flexible lengthy member and a second flexible lengthy member such that the first engagement part and the second engagement part are displaced as the first flexible lengthy member and the second flexible lengthy member move, the power transmission movable mechanism being configured such that the joint interlock displacement part is displaced by a displacement amount specified based on the amount of displacement of the first engagement part and the second engagement part, and a resultant force comprising of (or composed of) a force applied from the first flexible lengthy member and a force applied from the second flexible lengthy member to the first engagement part and the second engagement part, respectively, and a force applied from the joint mechanism to the joint interlock displacement part are balanced;

a control mechanism connected to an end of the first flexible lengthy member on an opposite side from the first engagement part, enabling the control mechanism to control the movement of the first flexible lengthy member; and an elastic structure engaged with the second flexible lengthy member such that the elastic structure generates an elastic force as the second flexible lengthy member moves (a first aspect of the invention).

According to the first aspect of the invention, the joint interlock displacement part of the power transmission movable mechanism is displaced according to a change in the amount of relative displacement of the first member and the second member caused by the motion of the joint mechanism. At this time, the movement of the first flexible lengthy member is controlled (e.g. braked) by the control mechanism so as to apply the elastic force of the elastic structure to the second engagement part of the power transmission movable mechanism through the intermediary of the second flexible lengthy member. Further, the tension imparted to the first flexible lengthy member by the control mechanism is applied to the first engagement part of the power transmission movable mechanism.

Thus, the resultant force of the forces applied to the first engagement per and the second engagement part as described above is imparted to the joint mechanism from the joint interlock displacement part. Hence, the resultant force comprising of the elastic force of the elastic structure and the force imparted to the first flexible lengthy member from the control mechanism can be imparted to the joint mechanism. With this arrangement, even if the elastic structure is small, sufficiently large joint power can be imparted to the joint mechanism.

Further, the power transmission movable mechanism installed between the elastic structure and the joint mechanism makes it possible to dispose the elastic structure so as to cause the elastic structure to be elastically deformed at a predetermined fixed position. In addition, the force from the control mechanism is transmitted to the first engagement part through the first flexible lengthy member and the force from the elastic structure is transmitted to the second engagement part through the second flexible lengthy member, thus permitting a higher degree of freedom of the placement of the elastic structure and the control mechanism.

Therefore, the first aspect of the invention makes it possible to impart sufficiently large power to the joint mechanism, which connects the two members, by using the elastic structure, and to achieve a reduction in the placement space or the like for the elastic structure.

The power transmission movable mechanism may adopt a variety of forms. For example, the power transmission movable mechanism may include a moving pulley, an outer periphery of which has a single flexible lengthy member, which is composed by connecting the first flexible lengthy member and the second flexible lengthy member into one, wound thereon and a bearing that supports the moving pulley such that the moving pulley is rotatable about its axis of rotation, both ends of a portion of the outer periphery of the moving pulley which is in contact with the single flexible lengthy member serving as the first engagement part and the second engagement part, and the bearing serving as the joint interlock displacement part a second aspect of the invention).

Alternatively, the power transmission movable mechanism includes, for example, a first rack and a second rack, which are disposed facing against each other and provided to be slidable in a same direction, a gear which is disposed between the first rack and the second rack and engaged with the first rack and the second rack, and a bearing which supports the gear such that the gear is rotatable about its axis of rotation, the first rack and the second rack serving as the first engagement part and the second engagement part, respectively, and the bearing serving as the joint interlock displacement part (a third aspect of the invention). The power transmission movable mechanism in the third aspect of the invention is, in other words, configured using a differential mechanism.

According to the second aspect or the third aspect of the invention, the configuration of the power transmission movable mechanism can be simplified.

In the first to the third aspects of the invention, the control mechanism may be configured to be capable of, for example, operating in at least a mode for preventing the first flexible lengthy member from moving and a mode for clearing the mode for the prevention (a fourth aspect of the invention).

With this arrangement, in the mode for preventing the first flexible lengthy member from moving, the large joint power can be imparted to the joint mechanism. In the mode in which the prevention mode has been released, a state in which the joint power imparted to the joint mechanism is sufficiently small or substantially zero can be accomplished.

In the first to fourth aspects of the invention, the elastic structure may be configured to have a first end to which the end of the second flexible lengthy member on the opposite side from the second engagement part is locked, and a second end provided to maintain a constant distance from a middle portion of a disposition path of the second flexible lengthy member along the disposition path, and to generate an elastic force according to elastic deformation between the first end and the second end (a fifth aspect of the invention).

This arrangement enables the elastic structure to be elastically deformed according to the movement of the second flexible lengthy member. Thus, an elastic force can be generated by the simple structure.

Further, in the first to the fourth aspects of the invention, the elastic structure may adopt a variety of forms. In this case, the elastic structure in particular is preferably an elastic structure formed to have a multilayer structure composed by alternately stacking a plurality of elastic members, each of which includes one or more hermetically sealed air chambers, volumes of which decrease by compression, and a plurality of partition plates having stiffness that is higher than that of the elastic members, a through hole being formed to extend in a direction of the stacking, a total length in the direction of the stacking being larger than a minimum width of each of the elastic members in a direction orthogonal to the direction of the stacking, and the second flexible lengthy member is inserted in the through hole of the elastic structure (a sixth aspect of the invention).

Further, in the fifth aspect of the invention, preferably, the elastic structure is formed to have a multilayer structure composed by alternately stacking a plurality of elastic members, each of which includes one or more hermetically sealed air chambers, volumes of which decrease by compression, and a plurality of partition plates having stiffness that is higher than that of the elastic members, a through hole being formed to extend in a direction of the stacking, and a total length in the direction of the stacking being larger than a minimum width of each of the elastic members in a direction orthogonal to the direction of the stacking, one end of both ends of the elastic structure in the direction of the stacking and the other end thereof are defined as the first end and the second end, respectively, and an end of the second flexible lengthy member on an opposite side from the second engagement part is inserted in the through hole from the second end of the elastic structure and locked to the first end of the elastic structure (a seventh aspect of the invention).

According to the sixth or the seventh aspect of the invention, despite its small size, the elastic structure is capable of generating a relatively large elastic force with high sensitivity by the compression thereof. Further, the elastic structure is comprising of the elastic members, which include the air chambers, as the major elements thereof, allowing the elastic structure to have a lighter weight.

Further, the elastic structure is configured to have the multilayer structure comprising of the plurality of the elastic members and the partition plates as described above. In addition, the second flexible lengthy member, to which a tension is imparted when the joint mechanism is actuated, is inserted in the through hole of the elastic structure. The arrangement makes it hard for an abnormal bending state to take place, typically represented by an excessive bend of the elastic structure when the elastic structure is compressed.

Hence, the compact, lightweight elastic structure is capable of stably generating the elastic force with high sensitivity by the compression.

Further, the seventh aspect of the invention makes it possible, by the simple configuration, to compress the elastic structure as the second flexible lengthy member moves.

The first to the seventh aspects of the invention may adopt, for example, the following application modes. The first member and the second member may be used as, for example, the members adapted to be attached to a person such that the first member and the second member move integrally with a thigh and a crus, respectively, of a leg of the person (an eighth aspect of the invention).

In this case, the placement space of the elastic structure and the like can be reduced. Further, the degree of freedom of the placement of the elastic structure and the control mechanism is higher. Thus, the elastic structure and the control mechanism can be easily attached to a person. Further, the small elastic structure can be used to impart sufficiently large joint power to the joint mechanism when a leg of a person is bent or stretched.

In the eighth aspect of the invention, preferably, the first member and the second member are comprising of frames adapted to be attached to a person such that the frames move integrally with a thigh and a crus, respectively, of a leg of the person, the elastic structure and the power transmission movable mechanism are installed to the frame constituting the first member, and the control mechanism is adapted to be attached to an upper body of the person (a ninth aspect of the invention).

With this arrangement, the elastic structure and the control mechanism can be disposed not to interfere with the motions of the legs of a person.

Further, in the eighth aspect and the ninth aspect of the invention, preferably, the joint mechanism includes a first link connected to the first member and the second member through an intermediary of joint shafts C1a, C1b in a pitch axis direction such that the first link is relatively rotatable in a pitch direction with respect to the first member and the second member; and a second link connected to the first member and the second member through the intermediary of joint shafts C2a, C2b in the pitch axis direction such that the second link is relatively rotatable in the pitch direction with respect to the first member and the second member, wherein the joint shafts C1a, C1b, C2a and C2b are disposed such that conditions (1) and (2) given below are satisfied (a tenth aspect of the invention).

Condition (1): The joint shaft C1b is positioned front side of the joint shaft C2b.

Condition (2): If an interval between the joint shaft C1a and the joint shaft C1b is denoted by D1, an interval between the joint shaft C2a and the joint shaft C2b is denoted by D2, an interval between the joint shaft C1a and the joint shaft C2a is denoted by Da, and an interval between the joint shaft C1b and the joint shaft C2b is denoted by Db, then a relationship expressed by D1>Da and D1+Db>D2+Da holds.

In the present invention, the pitch direction means the direction about the pitch axis of a person when the person wearing the first member and the second member is standing substantially upright. In this case, the pitch axis direction means the lateral direction of the person.

According to the tenth aspect of the invention, the relative displacement motions of the first member and the second member by the operation of the joint mechanism (i.e. the relative displacement motion corresponding to the bending or stretching motion of a leg of a person) can be accomplished in substantially the same manner as the bending or stretching motion between a thigh and a crus of the person.

Thus, when the person wearing the first member and the second member bends or stretches his or her leg, it is possible for the first member and the second member to be hardly relatively displaced with respect to the thigh and the crus of the leg of the person.

As a result, not only when a leg of the person is stretched but also when the leg is bent to a maximum, the joint mechanism can be prevented from jutting out to the front of the knee of the person.

Further, the matching between the motions of the first member and the second member and the motions of the thigh and the crus of a leg of a person is enhanced. This makes it possible to prevent or restrain the first member or the second member from rubbing against the thigh or the crus of the leg when the leg is bent or stretched.

In the tenth aspect of the invention, the joint interlock displacement part of the power transmission movable mechanism is preferably connected through the intermediary of a lengthy member to an outer periphery of a portion of the first link that is on the joint shaft C1a side (an eleventh aspect of the invention).

In the present invention, "the outer periphery of a portion of the first link that is on the joint shaft C1a side" means a portion of the first link that has an interval with respect to the joint shaft C1a (in other words, a portion that has a moment arm length relative to the joint shaft C1a).

In the joint mechanism according to the eleventh aspect of the invention, the amount of a change in the amount of displacement, i.e. the amount of rotation, of the first link when a leg of a person wearing the first member and the second member is bent to a maximum from a stretched state can be controlled to be relatively small. Hence, the required amount of displacement of the joint interlock displacement part of the power transmission movable mechanism connected to the outer periphery of the first link through the intermediary of the lengthy member can be controlled to be relatively small. Thus, the placement space for the power transmission movable mechanism can be reduced.

BRIEF DESCRIPTION OF THE DRAWINGS

FIG. 4 is a diagram illustrating the configuration and the operation of a knee joint mechanism of the motion assisting apparatus in the embodiment;

FIG. 5 is a diagram illustrating the configuration of a joint power control device of the motion assisting apparatus in the embodiment;

FIG. 8A to FIG. 8C are diagrams illustrating the operations performed when a person wearing the motion assisting apparatus in the embodiment bends or stretches his or her leg;

FIG. 9 is a diagram illustrating an example of the change characteristics of an assisting force generated by the motion assisting apparatus in the embodiment;

FIG. 13 is a diagram illustrating the configuration of a modification of a third example of the joint power control device;

FIG. 14 is a perspective view from the front side of a configuration example of a leg link mechanism of the motion assisting apparatus; and FIG. 15 is a perspective view from the rear side of the configuration example of the leg link mechanism of the motion assisting apparatus.

DESCRIPTION OF THE PREFERRED EMBODIMENTS

An embodiment of the present invention will be described below with reference to FIG. 1 to FIG. 9.

Figure 1:
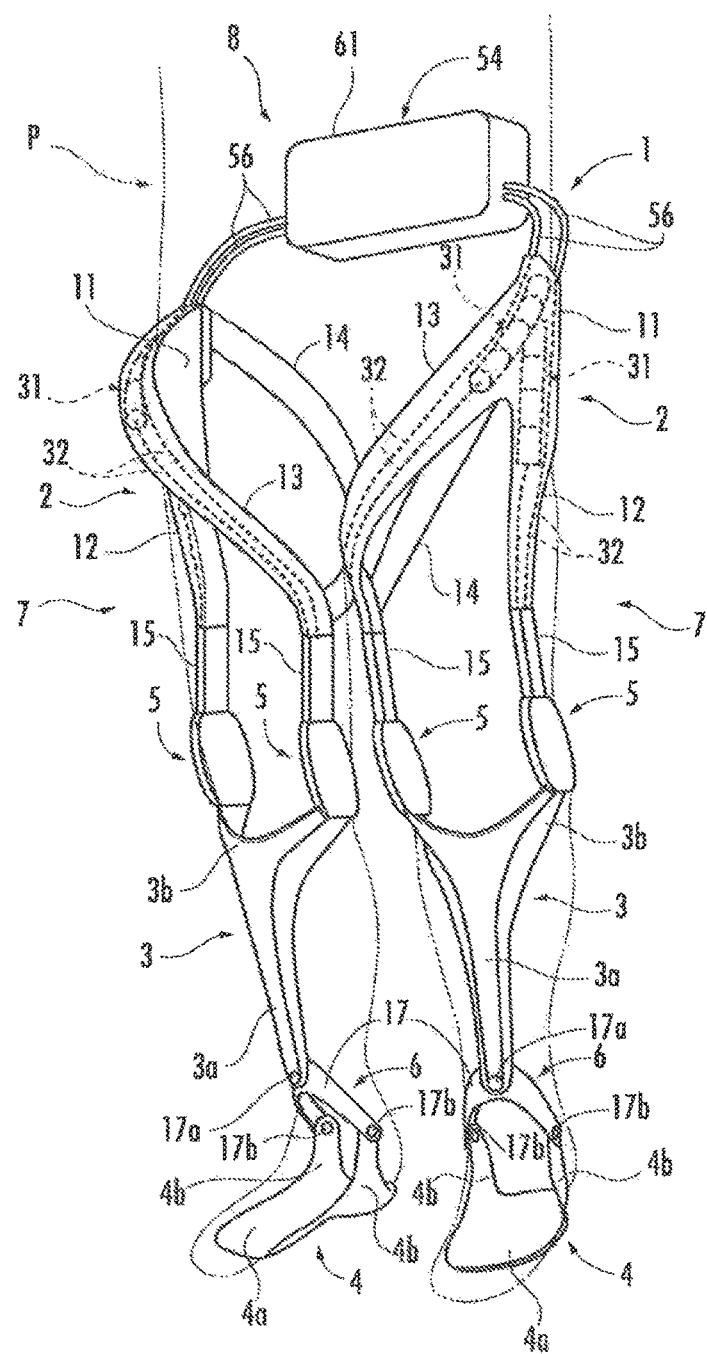
FIG. 1 is a perspective view from a front side of a motion assisting apparatus in an embodiment of the present invention.
Figure 2:
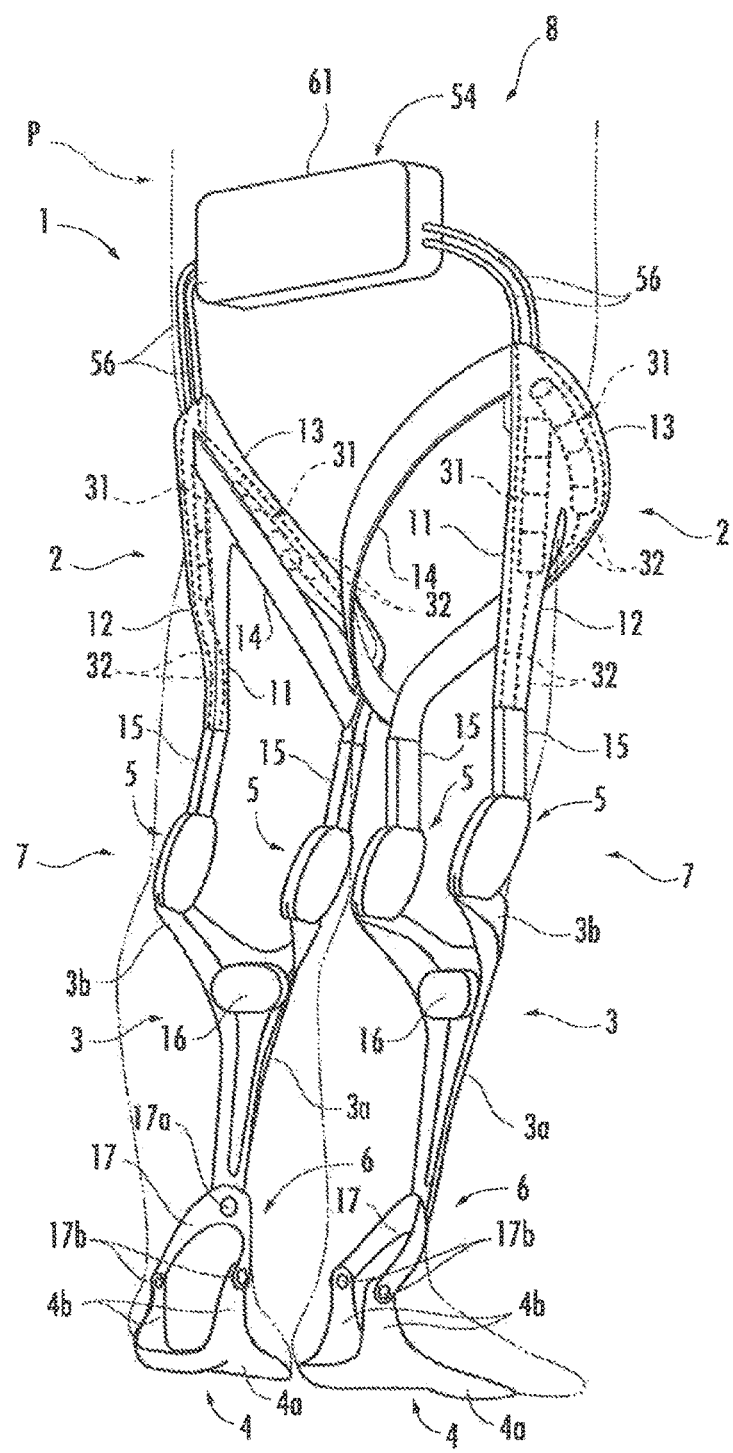
FIG. 2 is a perspective view from a rear side of the motion assisting apparatus in the embodiment.
Figure 3:
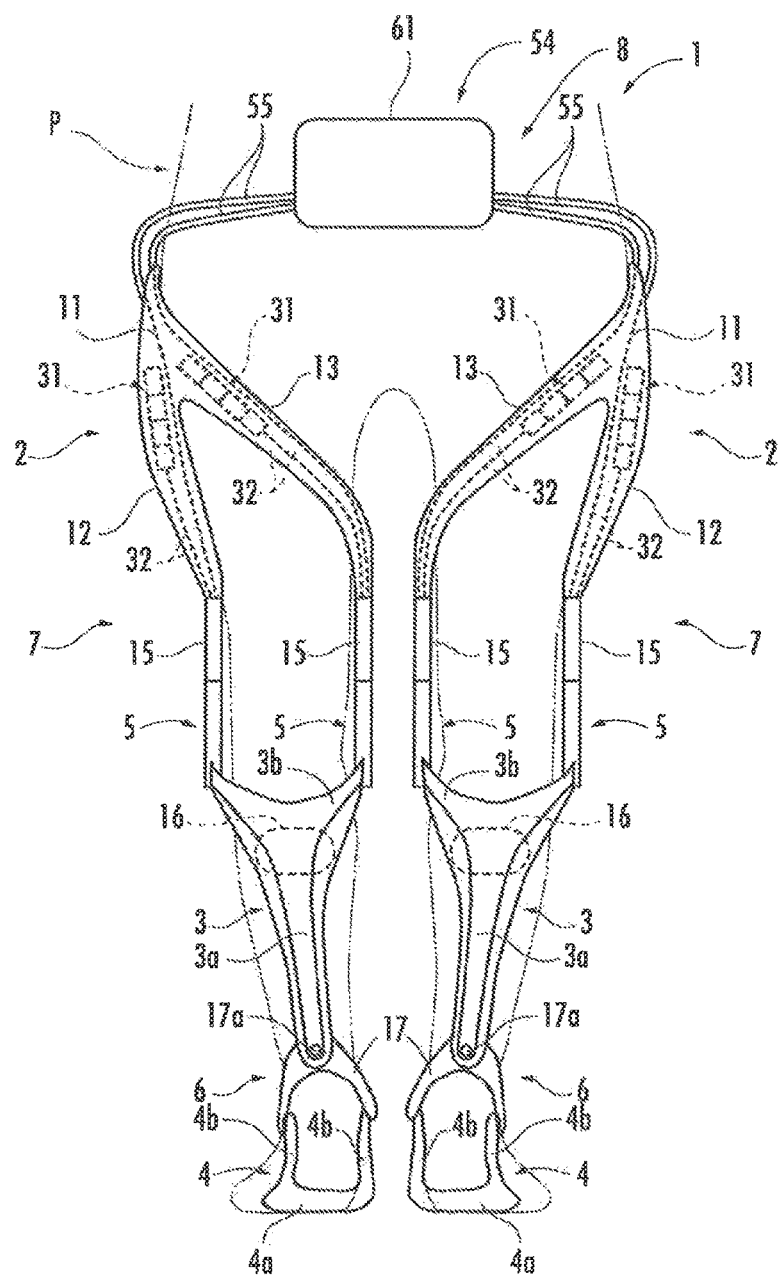
FIG. 3 is a front view of the motion assisting apparatus in the embodiment.

Referring to FIG. 1 to FIG. 3, a joint power control device 8 illustrated in the present embodiment is a device provided in a motion assisting apparatus 1 to be attached to a person to be assisted P in order to assist the motions of his or her legs mainly when the person to be assisted P walks.

The motion assisting apparatus 1 has, for each leg of the person to be assisted P, a leg link mechanism 7 that includes a thigh frame 2, a crus frame 3, a foot frame 4, and a pair of knee joint mechanisms 5, 5, which connect the thigh frame 2 and the crus frame 3 in a relatively displaceable manner, and an ankle joint mechanism 6, which connects the crus frame 3 and the foot frame 4 in a relatively displaceable manner, and a joint power control device 8 that controls a joint power, which is a force to be imparted to the knee joint mechanisms 5, 5 of the leg link mechanism 7. In the present embodiment, the thigh frame 2 and the crus frame 3 correspond to the first member and the second member, respectively, in the present invention, and the knee joint mechanism 5 corresponds to the joint mechanism in the present invention.

In FIG. 1 to FIG. 3, for the sake of simplicity, each of the knee joint mechanisms 5 is schematically illustrated in a box shape, and the specific configuration of the knee joint mechanism 5 is not illustrated.

The leg link mechanism 7 for each leg of the person to be assisted P is attached to the leg such that each of the thigh frame 2, the crus frame 3 and the foot frame 4 moves integrally with each of the thigh, the crus and the foot of the leg (the right leg or the left leg) to which the leg link mechanism 7 is attached.

The phrase "the thigh frame 2 integrally moves with the thigh of the leg" means that the thigh frame 2 moves together with the thigh of the leg such that the position and the attitude of the thigh frame 2 relative to the thigh of the leg are maintained to be constant or substantially constant. In this case, the position or the attitude of the thigh frame 2 relative to the thigh of the leg may be allowed to slightly change (the thigh frame is slightly relatively displaced relative to the thigh of the leg) with the motion of the leg. This applies also to the phrase "each of the crus frame 3 and the foot frame 4 moves integrally with each of the crus and the foot."

The paired knee joint mechanisms 5, 5 of each of the leg link mechanisms 7 are disposed on both sides (namely, on the outer side and the inner side of the knee) in a lateral direction (namely, in the direction of a pitch axis) of the knee of the leg of the person to be assisted P when the leg link mechanism 7 is attached to the leg of the person to be assisted P.

In the following description, of the knee joint mechanisms 5, 5, the knee joint mechanism 5 disposed on the outer side of the knee may be referred to as the "outer knee joint mechanism 5" and the knee joint mechanism 5 disposed on the inner side of the knee may be referred to as the "inner knee joint mechanism 5."

Further, in the description of the present embodiment, of both sides in the lateral direction of the leg, the inner side and the outer side of each portion (namely, the knee, the thigh, and the like) of each leg of the person to be assisted P means the side closer to the other leg, i.e. the side opposing the other leg, and the side farther from the other leg, respectively. In other words, the inner side and the outer side of the right leg of the person to be assisted P are the left side and the right side, respectively, of the right leg, and the inner side and the outer side of the left leg are the right side and the left side, respectively, of the left leg.

Further, the terms "inner" and "outer" may be added to the designation of each element to distinguish between the elements associated with the inner knee joint mechanism 5 and the elements associated with the outer knee joint mechanism 5.

Further, in the description of the present embodiment, unless otherwise specified, the lateral direction (or the direction of the pitch axis), the longitudinal direction (or the direction of a roll axis), and the vertical direction (or the direction of a yaw axis) mean the lateral direction, the longitudinal direction, and the vertical direction, respectively, of the person to be assisted P when the person to be assisted P wearing the motion assisting apparatus 1 is standing substantially in an upright posture. Further, the pitch direction, the roll direction and the yaw direction mean the direction of rotation in the direction about the pitch axis, the direction of rotation in the direction about the roll axis, and the direction of rotation in the direction about the yaw axis, respectively.

The thigh frame 2 has, as its base frames, a first element frame 12 and a second element frame 13, which are bifurcated and extended from a base 11. The first element frame 12 and the second element frame 13 are configured to be integral and made of, for example, a resin member that is relatively hard.

The first element frame 12 and the second element frame 13 may alternatively be formed of a structure made by combining a plurality of members together into one piece.

The base 11, which is the root portion of the first element frame 12 and the second element frame 13, in the present embodiment is a portion which is disposed on one side of the waist at a height that is equal to or greater than the height of the inner base of the leg (i.e. the portion where the inner surfaces of both legs intersect with each other) of the person to be assisted P and lower than the hipbone. The base 11 in the present embodiment provides the upper end portion of the thigh frame 2. In this case, properly setting the vertical length of the thigh frame 2 allows the base 11 (the upper end portion of the thigh frame 2) to be disposed at the foregoing height.

The term "one side of the waist" refers to the right side of the waist in association with the thigh frame 2 of the leg link mechanism 7 for the right leg of the person to be assisted P, or refers to the left side of the waist in association with the thigh frame 2 of the leg link mechanism 7 for the left leg.

The first element frame 12 is an element frame that connects the base 11 to the outer knee joint mechanism 5. The first element frame 12 is configured to extend along the outer surface of the thigh of the person to be assisted P from the base 11 in the direction of the length of the thigh to the outer knee joint mechanism 5.

The second element frame 13 is an element frame that connects the base 11 to the inner knee joint mechanism 5. The second element frame 13 is configured to extend from the base 11 to the inner knee joint mechanism 5, passing the front surface (i.e. curving toward the front surface side) of the thigh of the person to be assisted P.

Further, the second element frame 13 is configured to be inclined with respect to the thigh in the direction substantially toward the inner knee joint mechanism 5 from the base 11, as observed from the front side of the thigh of the leg of the person to be assisted P. In other words, the second element frame 13 is configured to extend to the inner knee joint mechanism 5 obliquely with respect to the thigh such that the second element frame 13 extends from the base 11 obliquely downward, as observed from the front side of the thigh of the leg of the person to be assisted P.

In this case, according to an example of the present embodiment, the second element frame 13 is configured such that the tilt of a portion thereof adjacent to the base 11 (namely, an upper portion) and a portion thereof adjacent to the inner knee joint mechanism 5 (namely, a lower portion) relative to the direction of length of the thigh (i.e. the tilt as observed from the front side of the thigh) becomes smaller than that of a middle portion and that the tilt continuously and smoothly changes.

Further, the second element frame 13 is formed in a curved shape so as to smoothly curve obliquely along the curved surface on the front side of the thigh.

Further, the first element frame 12 and the second element frame 13 in the present embodiment are formed to be hollow inside so as to make it possible to accommodate an elastic structure 31 and the like, which will be discussed later.

Further, each of the first element frame 12 and the second element frame 13 has, at the lower end portion thereof, a hollow joint connection 15, which is a portion to be connected to the knee joint mechanism 5. The joint connection 15 is fixed to the upper portion of each of the first element frame 12 and the second element frame 13 (i.e., fixed to a portion on the upper side from the joint connection 15), or formed integrally with the upper portion. The joint connections 15, 15 at the lower end portions of the first element frame 12 and the second element frame 13 extend in substantially the same direction, namely, in the direction of the length of the thigh.

Further, the first element frame 12 and the second element frame 13 are connected to the outer knee joint mechanism 5 and the inner knee joint mechanism 5, respectively, through the joint connections 15 at the lower end portions thereof. In the present embodiment, moving pulleys 51, which will be discussed hereinafter, are installed in the joint connections 15 at the lower end portions of the first element frame 12 and the second element frame 13.

In the following description, the joint connection 15 at the lower end portion of the first element frame 12 may be referred to as the outer joint connection 15, and the joint connection 15 at the lower end portion of the second element frame 13 may be referred to as the inner joint connection 15.

The thigh frame 2 further includes a body support member 14 extended over between the base 11 and the lower portion of the second element frame 13. The body support member 14 is a member that functions to support the thigh of the person to be assisted P from the back side. The body support member 14 is disposed such that the thigh of the person to be assisted P can be inserted between the body support member 14 and the second element frame 13.

To be specific, the body support member 14 is extended over between the base 11 and the lower portion of the second element frame 13 such that the body support member 14 extends obliquely relative to the thigh and curves along the back of the lower portion of the buttock and the thigh of the person to be assisted P, extending from the base 11 obliquely downward in the direction toward the lower portion of the second element frame 13, as observed from the back side of the thigh of the person to be assisted P. Further, one end portion of the body support member 14 is connected to the base 11, while the other end portion thereof is connected to a lower portion of the second element frame 13, i.e., connected to a portion slightly above the inner joint connection 15 in the illustrated example.

In this case, the tilt of the body support member 14 with respect to the direction of the length of the thigh, i.e. the tilt as observed from the front side or the back side of the thigh, is substantially the same as the tilt of the second element frame 13 in the present embodiment.

Further, in the present embodiment, the body support member 14 is formed in a relatively thin belt shape so as to permit minimized sensation provoked by the foreign object coming in contact with the thigh or the buttocks when, for example, the person to be assisted P sits on a chair. Further, the body support member 14 has stiffness that is lower than that of the first element frame 12 and the second element frame 13. The body support member 14 is comprising of, for example, a resin member or a fabric member or the like that is softer than the first element frame 12 and the second element frame 13.

The crus frame 3 in the present embodiment has a base portion 3a, which is disposed to extend in the direction of the length of the crus on the front side of the crus of the person to be assisted P, and a forked portion 3b, which is integrally formed with the base portion 3a such that it extends from the upper portion of the base portion 3a to both sides (namely, the outer side and the inner side) of the knee of the person to be assisted P.

Further, of a pair of the distal ends of the forked portion 3b, the distal end on the inner side of the knee is connected to the second element frame 13 of the thigh frame 2 through the intermediary of the inner knee joint mechanism 5. Further, the distal end on the outer side of the knee is connected to the first element frame 12 of the thigh frame 2 through the intermediary of the outer knee joint mechanism 5.

The upper portion of the base portion 3a (the base of the forked portion 3b), which has a relatively large area, is disposed to cover the upper front (specifically the tibial tuberosity) of the crus. The upper portion of the base portion 3a is the part to which the force of contact with the tibial tuberosity of the crus is applied when the leg of the person to be assisted P, for example, bends or stretches. Hence, a pad 16 comprising of a buffer member is fixed to the inner surface of the upper portion of the base portion 3a, as indicated by the dashed line in FIG. 3. Thus, the upper portion of the base portion 3a can be abutted against the tibial tuberosity of the person to be assisted P through the intermediary of the pad 16.

The foot frame 4 in the present embodiment is a plate-shaped frame having a bottom plate 4a, which is disposed on the bottom surface side of a foot of the person to be assisted P and on which the foot is rested. The bottom plate 4a is formed to have an insole shape that is substantially the same as a shoe insole shape or the shape of an insole with a part thereof cut off (e.g. the shape of an insole with a front part or a rear part thereof cut off).

Further, the foot frame 4 has rising portions 4b, 4b, which rise from both sides of a part of the bottom plate 4a that is adjacent to the heel. The rising portions 4b, 4b are connected to the lower end of the crus frame 3 (i.e. the lower end of the base portion 3a) through the intermediary of the ankle joint mechanism 6. The rising portions 4b, 4b are disposed to be positioned on the inner side and the outer side of the malleolus of the ankle of the person to be assisted P when the foot of the person to be assisted P is rested on the bottom plate 4a.

The ankle joint mechanism 6 includes a link member 17, which is disposed to encircle the front surrounding of the ankle of the person to be assisted P and which has a substantially semicircular shape (or a substantially U shape). A middle part of the link member 17 is connected to the lower end portion of the crus frame 3 through the intermediary of a joint shaft 17a in the direction of the roll axis.

Further, the link member 17 is pivotably supported such that the link member 17 can be relatively rotated in the roll direction about the axial center of the joint shaft 17a with respect to the crus frame 3.

The joint shaft 17a in the present embodiment is disposed to be positioned at a level that is higher than the lower joint of the talus of the ankle of the person to be assisted P when the foot of the person to be assisted P is placed on the bottom plate 4a of the foot frame 4. In the illustrated example, the joint shaft 17a is disposed to be positioned on the front side of the lower end portion of the crus of the person to be assisted P and above the instep of the foot.

Each of both ends of the link member 17 is connected to the rising portion 4b of the foot frame 4 through the intermediary of the joint shaft 17b in the direction of the pitch axis (more specifically, the rising portion 4b on the same inner or outer side of the heel of the person to be assisted P as the end portion of the link member 17). In this case, the joint shaft 17b on the inner side of the heel of the person to be assisted P and the joint shaft 17b on the outer side thereof are concentrically disposed. Further, the link member 17 is journaled such that the link member 17 can be relatively rotated with respect to the foot frame 4 about the axial centers of the joint shafts 17b and 17b on the inner side and the outer side (in the pitch direction).

The directions of the axial centers of the joint shafts 17b and 17b on the inner side and the outer side, respectively, will be supplementarily described. The rotational axes of the motions of the plantar flexion and the dorsiflexion of the ankle of the person to be assisted P are generally slightly inclined relative to a plane orthogonal to the direction of the long axis of the tibia bone (i.e. the direction of the length of the crus).

Therefore, in the present embodiment, the axial centers of the joint shafts 17b, 17b of the ankle joint mechanism 6 are slightly inclined relative to the plane orthogonal to the direction of the long axis of the tibia bone (i.e. the direction of the length of the crus) of the person to be assisted P such that the axial centers thereof agree as much as possible with the rotational axes of the motions of the plantar flexion and the dorsiflexion of the ankle of the person to be assisted P. In this case, the axial centers of the joint shafts 17b, 17b of the ankle joint mechanism 6 are inclined such that the joint shaft 17b on the outer side is slightly lower than the joint shaft 17b on the inner side when the bottom plate 4a of the foot frame 4 is placed on a horizontal surface (or when the person to be assisted P wearing the motion assisting apparatus 1 is standing on a horizontal surface).

Since the ankle joint mechanism 6 is configured as described above, at the time of the motions of the plantar flexion and the dorsiflexion of the ankle of the person to be assisted P, the crus frame 3 and the foot frame 4 move integrally with the crus and the foot, minimizing the chance of the occurrence of relative displacements thereof with respect to the crus and foot of the person to be assisted P.

Further, the joint shaft 17a in the direction of the roll axis of the ankle joint mechanism 6 is disposed above the instep of the foot of the person to be assisted P, thus preventing the foot from interfering with the joint shaft 17a at the time of the motion of the plantar flexion of the ankle.

In the present embodiment, the ankle joint mechanism 6 does not have a joint shaft in the direction of the yaw axis (i.e. the vertical direction). However, if the foot of the person to be assisted P is rotated in the yaw direction relative to the crus, then the base portion 3a of the crus frame 3 is twisted. This enables the foot frame 4 to relatively rotate in the yaw direction with respect to the crus frame 3. Hence, the person to be assisted P can move without an impediment his or her foot to an arbitrary attitude with respect to the crus.

Both the outer knee joint mechanism 5 and the inner knee joint mechanism 5 are joint mechanisms sharing the same construction. Each of the knee joint mechanisms 5 in the present embodiment is configured to make it possible to accomplish the bending and stretching motions of the leg link mechanism 7 (i.e. the relative displacement motion between the thigh frame 2 and the crus frame 3) by the motions of the knee joint mechanisms 5, 5 in the same motional manner as the bending and stretching motions of a leg (i.e. the relative displacement motion between the thigh and the lower end portion by the motions of the knee joint of an average person.

Referring to FIG. 4, the following will describe a specific configuration of, for example, the outer knee joint mechanism 5 as a representative of the outer knee joint mechanism 5 and the inner knee joint mechanism 5. FIG. 4 illustrates, in addition to the configuration of the knee joint mechanism 5, the changes of the state of the knee joint mechanism 5 when the leg link mechanism 7 is bent from a stretched state thereof.

The outer knee joint mechanism 5 has a first link 21 and a second link 22, which are two links connecting a thigh frame 2 (specifically, the first element frame 12) and a crus frame 3 (specifically, the outer distal end portion of the pair of the distal end portions of the forked portion 3b).

The first link 21 is connected to the joint connection 15 at the lower end portion of the first element frame 12 of the thigh frame 2 through a joint shaft 21a. The first link 21 is also connected to the outer distal end portion of the forked portion 3b of the crus frame 3 through a joint shaft 21b. The joint shafts 21a and 21b have axial centers in the direction of the pitch axis, which are parallel to each other. Further, the first link 21 is journaled so as to be relatively rotatable in the pitch direction about the axial center of the joint shaft 21a with respect to the thigh frame 2. The first link 21 is also journaled so as to be relatively rotatable in the pitch direction about the axial center of the joint shaft 21b with respect to the crus frame 3.

The second link 22 is connected to the joint connection 15 at the lower end portion of the first element frame 12 of the thigh frame 2 through a joint shaft 22a. The second link 22 is also connected to the outer distal end portion of the forked portion 3b of the crus frame 3 through a joint shaft 22b. The joint shafts 22a and 22b have axial centers, which are parallel to each other and in the same direction (namely, the direction of the pitch axis) as that of the axial centers of the joint shafts 21a, 21b. Further, the second link 22 is journaled so as to be relatively rotatable in the pitch direction about the axial center of the joint shaft 22a with respect to the thigh frame 2. The second link 22 is also journaled so as to be relatively rotatable in the pitch direction about the axial center of the joint shaft 22b with respect to the crus frame 3.

The joint shaft 21b of the first link 21 that is adjacent to the crus frame 3 and the joint shaft 22b of the second link 22 that is adjacent to the crus frame 3 are disposed such that the joint shaft 22b is positioned farther to the rear than the joint shaft 21b.

Further, in the present embodiment, if the bending angle between the thigh frame 2 and the crus frame 3 is zero degrees, i.e. when the leg link mechanism 7 is stretched, then the joint shaft 22a of the second link 22 that is adjacent to the thigh frame 2 is positioned slightly farther to the rear side than the joint shaft 21a of the first link 21 that is adjacent to the thigh frame 2.

Further, as illustrated in FIG. 4, in the total of four joint shafts 21a, 21b, 22a and 22b of the first link 21 and the second link 22, if the interval between the axial centers of the joint shafts 21a and 21b is denoted by D1, the interval between the axial centers of the joint shafts 22a and 22b is denoted by D2, the interval between the axial centers of the joint shafts 21a and 22a is denoted by Da, and the interval between the axial centers of the joint shafts 21b and 22b is denoted by Db, then these D1, D2, Da and Db are set such that the relationships of expressions (1a) to (1c) given below hold.

$$D1 > Da \quad (1a)$$

$$D1 + Db > D3 + Da \quad (1b)$$

$$Da < Db \quad (1c)$$

The first link 21 and the second link 22 are disposed such that the positions thereof in the lateral direction i.e. in the direction perpendicular to the paper surface of FIG. 4) are staggered so as not to interfere with each other when they are bent or stretched between the thigh frame 2 and the crus frame 3.

The above has described the detailed structure of the outer knee joint mechanism 5. The inner knee joint mechanism 5 has the same configuration as that of the outer knee joint mechanism 5. Further, in the inner knee joint mechanism 5, the joint connection 15 at the lower end portion of the second element frame 13 of the thigh frame 2 and the inner distal end portion of the forked portion 3b of the crus frame 3 are connected through the intermediary of the first link 21 and the second link 22.

In this case, the first link 21 of the inner knee joint mechanism 5 is journaled in a relatively rotatable manner by the joint connection 15 at the lower end portion of the second element frame 13 and the inner distal end portion of the forked portion 3b of the crus frame 3 through the intermediary of the joint shafts 21a and 21b, respectively.

Further, the second link 22 of the inner knee joint mechanism 5 is journaled in a relatively rotatable manner by the joint connection 15 at the lower end portion of the second element frame 13 and the inner distal end portion of the forked portion 3b of the crus frame 3 through the intermediary of the joint shafts 22a and 22b, respectively.

Further, the four joint shafts 21a, 21b, 22a and 22b in the inner knee joint mechanism 5 are disposed concentrically with the four joint shafts 21a, 21b, 22a and 22b, respectively, in the outer knee joint mechanism 5.

A supplementary description will be given of the directions of the axial centers of the four joint shafts 21a, 21b, 22a and 22b of each of the knee joint mechanisms 5. Preferably, the axial centers of the joint shafts 21a, 21b, 22a and 22b of each of the knee joint mechanisms 5 are slightly inclined with respect to the surface orthogonal to the direction of the long axis of the tibia bone, i.e. the direction of the length of the crus, in order for the thigh frame 2 and the crus frame 3 to integrally move with the thigh and the crus, respectively, of the person to be assisted P with a minimized chance of the occurrence of the relative displacement with respect to the thigh and the crus when a leg of the person to be assisted P bends or stretches.

Accordingly, in the present embodiment, the directions of the axial centers of the joint shafts 21a, 21b, 22a and 22b of each of the knee joint mechanisms 5 are slightly inclined with respect to the surface orthogonal to the direction of the length of the crus. In this case, the directions of the axial centers are inclined such that the joint shafts 21a, 21b, 22a and 22b of the inner knee joint mechanism 5 are lower than the joint shafts 21a, 21b, 22a and 22b, respectively, of the outer knee joint mechanism 5 when the person to be assisted P wearing the motion assisting apparatus 1 is standing on a horizontal surface.

Each of the inner knee joint mechanism 5 and the outer knee joint mechanism 5 is configured as described above. Hence, when the leg link mechanism 7 is bent or stretched at the knee joint mechanism 5, the first link 21 and the second link 22 of each of the knee joint mechanisms 5 move as the bending degree, i.e. the bending angle, of the crus frame 3 with respect to the thigh frame 2 increases, as illustrated in FIG. 4.

In this case, the first link 21 and the second link 22 of each of the knee joint mechanisms 5 move such that, as the bending angle of the crus frame 3 with respect to the thigh frame 2 increases from the angle in the state in which the leg link mechanism 7 is stretched (zero degrees), the upper joint shaft 21a of the first link 21 moves from a state in which the upper joint shaft 21a is positioned at the front side relative to the straight line connecting the joint shafts 22a and 22b of the second link 22, to a position at the rear side relative to the straight line via a state in which the upper joint shaft 21a is positioned on the straight line.

The motion of the knee joint mechanism 5 described above makes it possible to perform the relative displacement motion between the thigh frame 2 and the crus frame 3 in the bending or stretching motion of the leg link mechanism 7 in substantially the same manner as the relative displacement motion between the thigh and the crus in the bending or stretching motion of a leg of the person to be assisted P.

The leg link mechanisms 7 having the construction described above are attached to the person to be assisted P as illustrated in FIG. 1 and FIG. 2. In this case, each of the leg link mechanisms 7 is attached to the person to be assisted P by inserting the thigh of each leg of the person to be assisted P between the second element frame 13 of the thigh frame 2 of the leg link mechanism 7 corresponding to the leg and the body support member 14, and the foot of the leg is placed on the bottom plate 4a of the foot frame 4 such that the heel of the ankle of the leg is positioned between the pair of the rising portions 4b, 4b of the foot frame 4.

Thus, when the person to be assisted P wearing the leg link mechanisms 7 moves his or her legs, the thigh frame 2, the crus frame 3 and the foot frame 4 of each of the leg link mechanisms 7 attached to the legs move integrally with the thigh, the crus and the foot, respectively, of each of the legs.

FIG. 8A to FIG. 8C illustrate an example of the motion of each of the leg link mechanisms 7 when the person to be assisted P wearing the leg link mechanisms 7 bends his or her legs. FIG. 8A illustrates a state in which the person to be assisted P is standing upright (i.e. a state in which the legs are stretched), FIG. 8C illustrates a state in which the person to be assisted P is squatting (i.e. a state in which the legs are bent to a maximum), and FIG. 8B illustrates a state of the bent legs between the state of FIG. 8A and the state of FIG. 8C.

In each of the leg link mechanisms 7 according to the present embodiment, the motion of each of the knee joint mechanisms 5 having the constructions described above makes it possible to perform the relative displacement motion between the thigh frame 2 and the crus frame 3 in the bending or stretching motion of the leg link mechanism 7 in substantially the same manner as the relative displacement motion between the thigh and the crus in the bending or stretching motion of a leg of the person to be assisted P.

Hence, when the person to be assisted P bends or stretches his or her legs, the bending or stretching motion between the thigh frame 2 and the crus frame 3 is performed with a minimized chance of the occurrence of the relative displacements of the thigh frame 2 and the crus frame 3 with respect to the thigh and the cams, respectively, of each of the legs.

As a result, each of the knee joint mechanisms 5 is held at a position on the inner side or the outer side of the knee without jutting out to the front side of the knee from the position on the inner side or the outer side of the knee when the bending degree of the leg of the person to be assisted P is small and even when the bending degree is increased to a large degree, as seen by referring to FIG. 8A to FIG. 8C. Furthermore, even when the person to be assisted P kneels down, the knee joint mechanisms 5 will not come in contact with a floor, getting in the way.

Alternatively, the knee joint mechanism between the thigh frame 2 and the cams frame 3 can be comprising of, for example, a joint mechanism of a single-axis structure having the degree of freedom of rotation about one axis in the direction of the pitch axis.

In this case, however, the mismatch between the motion of the knee joint mechanism and the motion of the knee joint of a leg of time person to be assisted P tends to cause the relative displacements of the thigh frame 2 and the crus frame 3 with respect to the thigh and the crus, respectively, when the person to be assisted P bends the leg. This is apt to cause the person to be assisted P to feel his or her thigh and the crus being rubbed against the thigh frame 2 and the crus frame 3, respectively.

Further, the relative displacements of the thigh frame 2 and the crus frame 3 with respect to the thigh and the crus, respectively, cause the knee joint mechanism to jut out to the front side of the knee of the person to be assisted P especially when the bending degree of the leg of the person to be assisted P is increased. Hence, when the person to be assisted P tries to kneel down, the knee joint mechanism comes in contact with a floor, frequently getting in the way. The knee joint mechanisms 5 according to the present embodiment make it possible to obviate such an inconvenience.

If a footwear, such as a shoe or a slipper, is put on a foot of the person to be assisted P, then a mode may be adopted, in which, for example, the foot of the person to be assisted P with the footwear on is placed on the bottom plate 4a of the foot frame 4. An alternative mode may be adopted, in which the foot of the person to be assisted P is placed on the bottom plate 4a of the foot frame 4 and then the footwear is put on the bottom plate 4a and the foot. Further, the foot frame 4 may be combined with the footwear into one piece, i.e. making the foot frame 4 as part of the footwear.

The joint power control device 8 will now be described in detail. The joint power control device 8 corresponding to each of the leg link mechanisms 7 of the motion assisting apparatus 1 includes two elastic structures 31, 31 configured to generate an elastic force by compression, flexible lengthy members 32 disposed, penetrating the elastic structures 31, and a tension imparting mechanism 33 which variably imparts tensions to the flexible lengthy members 32, as illustrated in FIG. 5.

In FIG. 5, the outer knee joint mechanism 5 and the inner knee joint mechanism 5 are laterally arranged, with the joint slats 21a, 21b, 22a, and 22b facing in a direction perpendicular to the paper surface.

The flexible lengthy members 32 in the present embodiment are wires (linear members), and will be hereinafter referred to as "the wires 32." The wires 32 correspond to the first flexible lengthy member and the second flexible lengthy member, which are connected into one member, in the present invention.

One of e elastic structures 31, 31 is an elastic structure that generates an elastic force providing a joint power to be imparted to the outer knee joint mechanism 5 (hereinafter may be referred to as "the outer elastic structure 31"), while the other thereof is an elastic structure that generates an elastic force providing a joint power to be imparted to the inner knee joint mechanism 5 (hereinafter may be referred to as "the inner elastic structure 31"). The outer elastic structure 31 and the inner elastic structure 31 share the same construction. An example of the construction will be described with reference to FIG. 6A, FIG. 6B and FIG. 6C.

Each of the elastic structures 31 is a multilayer structure composed by alternately stacking a plurality of elastic members 41 and a plurality of partition plates 42. Further, a through hole 43, which penetrates the elastic structure 31 in the direction of stacking the elastic members 41 and the partition plates 42, is formed at the axial center of the elastic structure 31.

Each of the elastic members 41 in the present embodiment is formed in a cylindrical shape and is comprising of an elastic member incorporating many hermetically sealed air chambers (not illustrated), such as, for example, a closed-cell (closed-pore) rubber sponge. In this case, the direction of the axial center of each of the elastic members 41 is the stacking direction of the elastic structure 31. Further, the through hole of each of the elastic members 41 constitutes a part of the through hole 43 of the elastic structure 31.

Further, the minimum width of the elastic member 41 (the minimum value of the external width of the elastic member 41 in the direction orthogonal to the direction of the axial center of the elastic member 41) is set to be smaller than the full length in the stacking direction of the elastic structure 31.

Figure 6A:
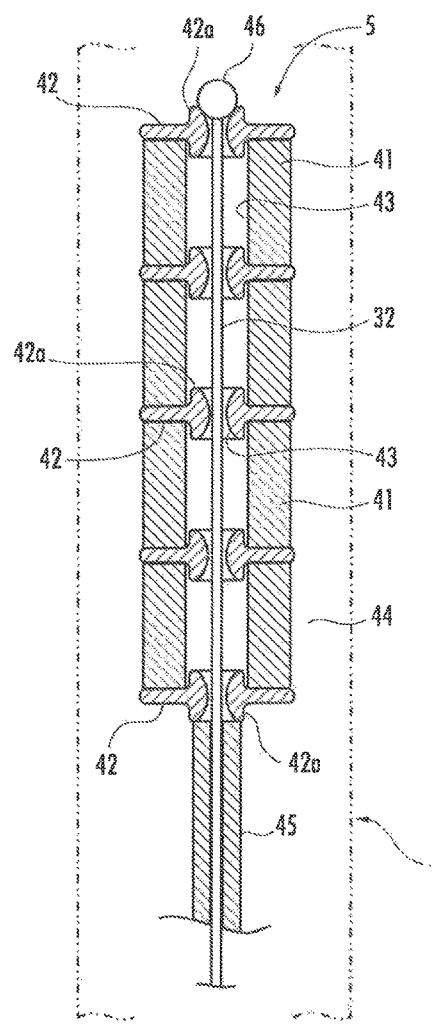
FIG. 6A is a sectional view of an elastic structure provided in the joint power control device illustrated in FIG. 5.
Figure 6B:
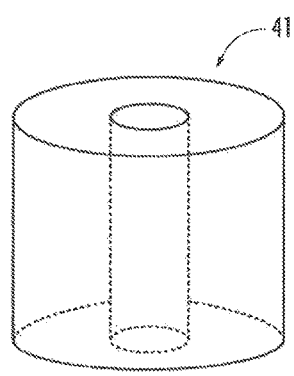
FIG. 6B is a perspective view illustrating an example of an elastic member provided in the elastic structure.

As an example, each of the elastic members 41 can be formed to have a cylindrical shape in a non-compressed state, i.e. in its natural state, as illustrated in FIG. 6B. In this case, the outside diameter (diameter) of the elastic member 41 is constant or substantially constant in the direction of the axial center of the elastic member 41, so that the outside diameter of the elastic member 41 coincides or substantially coincides with the minimum width and the maximum width of the elastic member 41. In this case, therefore, setting the outside diameter of the elastic member 41 to be smaller than the full length in the stacking direction of the elastic structure 31 makes the minimum width of the elastic member 41 smaller than the full length in the stacking direction of the elastic structure 31.

Each of the partition plates 42 is formed in an annular shape and comprising of a member having stiffness that is sufficiently higher than that of the elastic members 41, such as a metal or a hard resin. In this case, the direction of the axial center of each of the partition plates 42 (or the direction of the thickness thereof) is the stacking direction of the elastic structure 31. Further, the through hole of each of the partition plates 42 constitutes a part of the through hole 43 of the elastic structure 31.

The external shape and the area of each of the partition plates 42 observed in the direction of the axial center thereof, i.e. the direction of the thickness thereof, are set such that the entire or substantially entire end surface in the direction of the axial center of the elastic member 41 can be brought in contact with the end surface in the direction of the axial center of the partition plate 42, i.e. the surface on which the elastic member 41 is stacked.

Figure 6C:
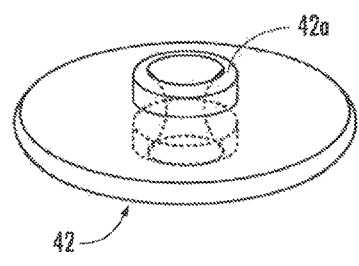
FIG. 6C is a perspective view illustrating an example of a partition plate provided in the elastic structure.

As an example, each of the partition plates 42 may be formed in the annular shape, as illustrated in FIG. 6C. Further, the outside diameters (diameters) of the partition plates 42 are set to coincide or substantially coincide with, for example, the outside diameters of the cylindrical elastic members 41, as illustrated in FIG. 6A.

Further, in the present embodiment, a portion 42a of each of the partition plates 42 that is adjacent to the inner periphery around the through hole is formed to be thicker than a portion surrounding the portion 42a, i.e. a portion adjacent to the outer circumference, as illustrated in FIG. 6C. The portion 42a (hereinafter referred to as "the thick portion 42a") projects to both sides in the direction of the thickness, i.e. the direction of the axial center, of the partition plate 42. Further, the thick portion 42a of each of the partition plates 42 is formed in a shape and a size that allows itself to be inserted in the end of the through hole of the elastic member 41 to be stacked on the partition plate 42.

For example, if the elastic members 41 are cylindrical, then the thick portion 42a of each of the partition plates 42 may be formed such that the external shape thereof (a circular shape in the illustrated example) observed in the direction of the axial center of the partition plate 42 is accommodated inside the cross-sectional shape of the through hole of the elastic member 41 (the shape thereof at the cross section orthogonal to the direction of the axial center of the elastic member 41), as illustrated in FIG. 6C. In this case, the maximum width (the diameter in the illustrated example) of the thick portion 42a is set to be slightly smaller than the width, i.e. the inside diameter, of the through hole of the elastic member 41.

Further, in the present embodiment, the minimum value of the cross-sectional area of the through hole of each of the partition plates 42, i.e. the area thereof at the cross section orthogonal to the direction of the axial center of the partition plate 42, is set to be smaller than the minimum value of the cross-sectional area of the through hole of the elastic member 41, i.e. the area thereof at the cross section orthogonal to the direction of the axial center of the elastic member 41).

In the present embodiment, the inner circumferential surface of the through hole of each of the partition plates 42 is formed in a curve such that the cross-sectional area of the through hole changes in the direction of the axial center, as illustrated in FIG. 6C.

More specifically, the inner circumferential surface of the through hole of the partition plate 42 is formed in a curve such that the cross-sectional area of the through hole of the partition plate 42 becomes a minimum at a middle position or substantially the central position between both ends (specifically, both ends in the direction of the axial center) of the thick portion 42a of the partition plate 42 and that the cross-sectional area of the through hole of the partition plate 42 increases toward both ends of the thick portion 42a of the partition plate 42. In other words, the inner circumferential surface of the through hole of the partition plate 42 is formed in a curve so as to be narrowed at the middle position in the direction of the axial center.

Further, the through hole of the elastic member 41 may be formed such that, for example, the cross-sectional area thereof remains constant in the direction of the axial center. In this case, minimum value of the cross-sectional area of the through hole of the partition plate 42, i.e. the cross-sectional area thereof at the middle position in the direction of the axial center of the partition plate 42, is set to be smaller than the constant cross-sectional area of the through hole of the elastic member 41.

Further, the inner circumferential surface of the through hole of the partition plate 42 is made of a slide material in order to reduce the coefficient of friction between the inner circumferential surface and the wire 32. As the slide material, a fluororesin, a copper alloy (phosphor bronze, brass or the like), or an oil-impregnated metal or the like may be used.

The elastic members 41 and the partition plates 42, which are configured as described above, are alternately stacked in a substantially coaxial manner thereby to constitute the elastic structure 31. In this case, the thick portion 42a of each of the partition plates 42 is inserted in the end of the through hole of the elastic member 41 stacked on the partition plate 42. Further, the through hole 43 of the elastic structure 31 is formed as the hole constituted by the through holes of the elastic members 41 and the through holes of the partition plates 42, which are in communication with each other.

Further, the contact surfaces of the elastic member 41 and the partition plate 42 that are stacked are firmly fixed to each other by, for example, an adhesive agent. More specifically, the contact surfaces are an end surface of the elastic member 41 and the end surface of the partition plate 42 in the direction of the thickness of the portion thereof adjacent to the outer circumference around the thick portion 42a, i.e. the portion that is thinner than the thick portion 42a. The stacked partition plate 42 and the elastic member 41 may be firmly fixed by a method other than bonding. For example, the stacked partition plate 42 and the elastic member 41 may be firmly fixed by, for example, baking or may be integrally molded.

In the present embodiment, the wire 32 is inserted in the through hole 43 of each of the elastic structures 31 configured as described above, and a tension is imparted to the wire 32, as will be described hereinafter. With the tension imparted to the wire 32 inserted in the through hole 43 as described above, each of the elastic structures 31 is compressed in the stacking direction. The elastic structure 31 generates an elastic force in the expanding direction according to the compression. The elastic force increases as the degree of the compression of the elastic structure 31 increases.

In this case, each of the elastic members 41 is constructed to have many hermetically sealed air chambers, as in, for example, a closed-cell (closed-pore) rubber sponge, so that each of the elastic members 41 generates, in addition to the elastic force generated by the material thereof, an elastic force generated by the compression (i.e. die reduction in volume) of the plurality of the air chambers in the elastic member 41 (more specifically, the elastic force generated by an increase in the air pressure in the air chambers caused by a reduction in the volume of each of the air chambers). This enables the elastic structures 31 to increase the elastic forces with high sensitivity by the compression in the direction of the axial center thereof.

Further, according to the present embodiment, the elastic structure 31 is formed to have the multilayer structure comprising of a plurality of elastic members 41 and the partition plates 42, and the wire 32 to which a tension is imparted is inserted in the through hole 43 of the elastic structure 31. This arrangement prevents the occurrence of an abnormal bending state in which the entire elastic structure 31 is excessively bent or the bending direction differs at each local spot in the stacking direction of the elastic structure 31 when the elastic structure 31 is compressed.

Further, although the wire 32 easily deflects from the center of the through hole 43 when the elastic structure 31 is compressed, the minimum value of the cross-sectional area of the through hole of each of the partition plates 42 according to the present embodiment is smaller than the minimum value of the cross-sectional area of the through hole of each of the elastic members 41. This prevents the wire 32 from coming in slide contact with the inner peripheral surface of the through hole of each of the elastic members 41. It is possible, therefore, to prevent the occurrence of the friction between the inner peripheral surface of the through hole of the elastic member 41 and the wire 32.

In addition, the inner peripheral surface of the through hole of the partition plate 42 is formed of a slide material, so that, even if the wire 32 comes in slide contact with the inner peripheral surface of the through hole of the partition plate 42, the force of the friction between the wire 32 and the partition plate 42 is minimized.

Further, the elastic member 41 and the partition plate 42 that are stacked are fixed to each other at their contact surfaces. Therefore, no friction between the contact surfaces will occur when the elastic structure 31 is elastically deformed.

This arrangement permits maximized prevention of the elastic energy accumulated by the compression of the elastic structure 31 from being wasted as heat energy generated by the friction.

Further, the portion adjacent to the inner periphery around the through hole in the partition plate 42 is formed to be the thick portion 42a, and the inner peripheral surface of the through hole on the inner side of the thick portion 42a is curved as described above. Hence, even if the wire 32 comes in contact with the inner peripheral surface of the through hole of the partition plate 42 when the elastic structure 31 is subjected to compression or the like, the contact pressure is dispersed in the direction of the length of the through hole of the partition plate 42. This prevents the pressure of contact between the wire 32 and the partition plate 42 from being concentrated on a local spot of the wire 32. As a result, the occurrence of breakage, damage or the like of the wire 32 can be prevented, thus permitting enhanced durability of the wire 32.

In the present embodiment, the elastic structure 31 configured as described above is installed to an appropriate place of the leg link mechanism 7, such as the thigh frame 2. More specifically, the outer elastic structure 31 and the inner elastic structure 31 are accommodated inside the first element frame 12 of the thigh frame 2 and inside the second element frame 13, respectively, as indicated by the dashed lines in FIG. 1 to FIG. 3.

In this case, each of the elastic structures 31 permits a bend to a certain extent due to the elastic deformation of the elastic members 41. Hence, if the place where the elastic structure 31 is to be installed in the first element frame 12 or the second element frame 13 is bent to a certain extent, then the elastic structure 31 can be installed to the installation place by being curved to fit the shape of the bent installation place. For example, in the motion assisting apparatus 1 according to the present embodiment, the inner elastic structure 31 is housed inside the second element frame 13 in the slightly curved state along the curved shape of the second element frame 13, as illustrated in FIG. 1 or FIG. 2.

The tension imparting mechanism 33 variably imparts a tension to the wire 32 inserted in the through hole 43 of each of the elastic structures 31.

In this case, the tension imparting mechanism 33 is configured to transmit the force between the wire 32 and the elastic structure 31 so as to cause the elastic structure 31 to generate an elastic force based on the tension imparted to the wire 32 inserted in the through hole 43 of the elastic structure 31 (an elastic force that balances the tension). Further, the tension imparting mechanism 33 is configured to be capable of changing the tension imparted to the wire 32 and the elastic force of the elastic structure 31 according to the relative displacement between the thigh frame 2 and the crus frame 3 (i.e. the bending or stretching motion of the leg link mechanism 7 caused by the motion of the knee joint mechanism 5). Further, the tension imparting mechanism 33 is configured to be also capable of imparting the elastic force of the elastic structure 31 as the joint power to the knee joint mechanism 5.

According to the present embodiment, the tension imparting mechanism 33 having the functions described above includes: a mechanism that binds a portion of the wire 32 led out from one end of the both ends in the direction of the axial center of each of the elastic structures 31 (hereinafter may be referred to as "the one-end-side led out portion") to one end of the elastic structure 31 thereby to maintain a constant length of the one-end-side led out portion; a mechanism that maintains a constant distance between a middle portion of the disposition path of a portion of the wire 32 led out from the other end of each of the elastic structures 31 (hereinafter may be referred to as "the other-end-side led out portion") and the other end of the elastic structure 31 along the disposition path; and a mechanism that transmits a relative displacement motion (the bending or stretching motion) of the crus frame 3 with respect to the thigh frame 2 to the other-end-side led out portion in order to cause the other-end-side led out portion of the wire 32 to move with respect to time other end of the elastic structure 31 according to time relative displacement motion.

In the present embodiment, the one end of each of the elastic structures 31 refers to the upper end of the elastic structure 31 (i.e. the end on the opposite side from the end closer to the knee joint mechanism 5), and the other end of the elastic structure 31 refers to the lower end of the elastic structure 31 (i.e. the end closer to the knee joint mechanism 5).

A specific exemplary configuration of the tension imparting mechanism 33 will be described below. Referring to FIG. 5, the tension imparting mechanism 33 in the present embodiment includes, as a constituent element of a mechanism which maintains a constant distance along a disposition path of the other-end-side led out portion of the wire 32 between a middle portion of the disposition path and the lower end (the other end) of the elastic structure 31, long thin tubes 45, one of which is disposed between a partition plate 42 at the lower end of the outer elastic structure 31 and a partition wall 15a at the upper end of the outer joint connection 15 in the first element frame 12 and the other of which is disposed between the partition plate 42 at the lower end of the inner elastic structure 31 and the partition wall 15a at the upper end of the inner joint connection 15 in the second element frame 13. In this case, the partition wall 15a of each of the joint connections 15 corresponds to the middle portion (a portion on the way) of the disposition path of the other-end-side led out portion of the wire 32.

Each of the tubes 45 is a guide tube in which the other-end-side led out portion of the wire 32 from the elastic structure 31 corresponding to the tube 45 is movably inserted.

One end of each of the tubes 45 is brought in contact with or fixed to the peripheral end portion of the opening end of the through hole of the partition plate 42 at the lower end of the elastic structure 31, and the other end of the tube 45 is brought in contact with or fixed to a predetermined portion of the partition wall 15a at the upper end of the joint connection 15. Each of the tubes 45 may alternatively be fixed to the thigh frame 2 (i.e. the first element frame 12 or the second element frame 13).

The inside of each of the tubes 45 is in communication with the through hole 43 of the elastic structure 31. The inside of the tube 45 is also in communication with the inside of the joint connection 15 through a hole formed in the partition wall 15a of the joint connection 15.

Further, the other-end-side led out portion of the wire 32 from each of the elastic structures 31 is inserted in the tube 45 connected to the lower end of the elastic structure 31. The other-end-side led out portion of the wire 32 is passed through the inside of the tube 45 to be led into the joint connection 15.

Each of the tubes 45 is comprising of, for example, a highly stiff member (e.g. a metal, a hard resin or the like). Hence, the distance between the lower end (the other end) of the outer elastic structure 1 and the partition wall 15a of the outer joint connection 15 (i.e. the distance along the disposition path of the wire 32) is maintained to be constant by the tube 45 between the outer elastic structure 31 and the partition wall 15a of the outer joint connection 15.

Similarly, the distance between the lower end (the other end) of the inner elastic structure 31 and the partition wall 15a of the inner joint connection 15 (i.e. the distance along the disposition path of the wire 32) is maintained to be constant by the tube 45 between the inner elastic structure 31 and the partition wall 15a of the inner joint connection 15.

Supplementarily, the tubes 45 may use tubes that have relatively low stiffness (i.e. have flexibility) against a bending load as long as the tubes exhibit high stiffness against a compression load in the direction of the length thereof.

Further, the mechanism that maintains the distance between the middle portion of the disposition path of the other-end-side led out portion of the wire 32 and the lower end, i.e. the other end, of the elastic structure 31 to be constant (i.e. the distance along the disposition path of the wire 32) is obviously not limited to the tubes 45 and may alternatively adopt a variety of configurations. For example, a configuration may be adopted, in which the partition plate 42 at the lower end of the outer elastic structure 31 and the partition plate 42 at the lower end of the inner elastic structure 31 may be directly fixed or immovably locked to the first element frame 12 and the second element frame 13, respectively. In this case, the tubes 45 may have low stiffness, i.e. may be soft. Alternatively, the tubes 45 may be omitted.

Further, the tension imparting mechanism 33 has a spherical lock member 46 fixed to the end of the one-end-side led out portion of the wire 32. The spherical lock member 46 is a constituent element of a mechanism that binds the one-end-side led out portion of the wire 32 from each of the elastic structures 31 to the upper end, i.e. the one end, of the elastic structure 31 in order to maintain a constant length of the one-end-side led out portion. The spherical lock member 46 has a diameter that is larger than the opening of the through hole 43 at the upper end, i.e. the one end, of the elastic structure 31. The lock member 46 is in contact with or fixed to the opening end peripheral portion of the through hole of the partition plate 42 at the upper end of the elastic structure 31.

Thus, in a state in which a tension is being imparted to the wire 32 by pulling the other-end-side led out portion of the wire 32 from the elastic structure 31, the wire 32 is locked to the partition plate 42 at the upper end of the elastic structure 31 through a lock member 46. Hence, the one-end-side led out portion of the wire 32 is bound to the upper end of the elastic structure 31 so as to maintain the length of the one-end-side led out portion of the wire 32 to be constant (substantially zero in this example).

Supplementarily, the mechanism for binding the one-end-side led out portion of the wire 32 to the upper end (the one end) of the elastic structure 31 in order to maintain the length of the one-end-side led out portion of the wire 32 to be constant is not limited to the foregoing lock member 46, and may adopt a variety of configurations. For example, the shape of the lock member 46 is not limited to the spherical shape and may be various other shapes, such as a disc shape. Further, a configuration may be adopted, in which the one-end-side led out portion of the wire 32 is fixed to the partition plate 42 at the upper end (the one end) of the elastic structure 31 through an appropriate fastening member or an adhesive or the like.

The wire 32 inserted in the through hole 43 of the elastic structure 31 as described above is bound to the upper end (the one end) of the elastic structure 31 so as to maintain the length of the one-end-side led out portion of the wire 32 to be constant by the lock member 46. Further, the tube 45 maintains a constant distance between the partition wall 15a of the joint connection 15, which is a middle portion (on a way portion) of the disposition path of the other-end-side led out portion of the wire 32, and the lower end (the other end) of the elastic structure 31 (i.e. the distance along the disposition path of the wire 32).

Thus, when the tension imparted to the wire 32 to pull the other-end-side led out portion of the wire 32 from the elastic structure 31 is increased, a compression load in the direction of the axial center of the elastic structure 31 is imparted to the elastic structure 31 from the wire 32. At this time, the elastic structure 31 is compressed as the other-end-side led out portion of the wire 32 moves with respect to the lower end of the elastic structure 31 in the direction in which the pull-out amount increases. This causes the elastic structure 31 to generate an elastic force that balances the tension of the wire 32.

The tension imparting mechanism 33 further includes a power transmission movable mechanism 53 comprising of a moving pulley 51, which is installed to each of the joint connections 15, and a bearing 52, which rotatably supports the moving pulley 51 about the axis of rotation thereof, and an actuator device 54 for controlling the first link 21 of each of the knee joint mechanisms 5 and the running operation of the wires 32. The power transmission movable mechanism 53 and the actuator device 54 are the constituent elements of a mechanism that transmits the relative displacement motion, i.e. the bending or stretching motion, of the crus frame 3 with respect to the thigh frame 2 to the other-end-side led out portion of the wire 32 from the elastic structure 31 such that the other-end-side led out portion moves with respect to the lower end, i.e. the other end, of the elastic structure 31 according to the relative displacement motion. In the following description, the moving pulley 51 installed to the outer joint connection 15 may be referred to as "the outer moving pulley 51," and the moving pulley 51 installed to the inner joint connection 15 may be referred to as "the inner moving pulley 51."

The actuator device 54 corresponds to the control mechanism in the present invention.

The outer moving pulley 51 is housed, together with the bearing 52 supporting the outer moving pulley 51, in the outer joint connection 15 such that the moving pulley 51 is translationally movable in the directions toward or away from the first link 21 of the outer knee joint mechanism 5

(the directions indicated by arrow Y1 in FIG. 5). Similarly, the inner moving pulley 51 is housed, together with the bearing 52 supporting the inner moving pulley 51, in the inner joint connection 15 such that the moving pulley 51 is translationally movable in the directions toward or away from the first link 21 of the inner knee joint mechanism 5 (the directions indicated by arrow Y2 in FIG. 5).

The directions in which the moving pulleys 51 and the bearings 52 can move are restricted by, for example, the inner wall surfaces of the joint connections 15 in which the moving pulleys 51 and the bearings 52 are housed.

Further, the bearing 52 for each of e moving pulleys 51 is connected to the first link 21 of the knee joint mechanism 5 through a wire 55, which is an example of the lengthy member, such that the bearing 52 is displaced, i.e. translationally moved, according to the relative displacement motion, i.e. the bending or stretching motion, of the crus frame 3 with respect to the thigh frame 2.

In this case, according to the present embodiment, the first link 21 is formed such that the outer peripheral portion thereof (in other words, the portion having an interval, i.e. a moment arm length, relative to the joint shaft 21a) functions as the outer peripheral portion of the pulley. Further, one end of the wire 55 on the first link 21 side is fixed to the outer peripheral portion of the first link 21. Further, the other end of the wire 55 is locked or fixed to the bearing 52.

With this arrangement, the first link 21 of each of the knee joint mechanisms 5 rotates about the axial center of the joint shaft 21a with respect to the thigh frame 2 according to the relative displacement motion of the crus frame 3 with respect to the thigh frame 2 (i.e. the bending or stretching motion of the leg link mechanism 7). As a result, the amount of winding of the wire 55 at the first link 21 increases or decreases.

Thus, on the outer side and the inner side, the moving pulleys 51 and the bearings 52 translationally move toward or away from the first links 21 of the knee joint mechanisms 5 according to the relative displacement motions of the crus frames 3 with respect to the thigh frames 2, in this case, according to the present embodiment, the amount of winding of the wire 55 at each of the first links 21 increases as the bending degree of each of the crus frames 3 with respect to each of the thigh frames 2 increases. This causes each of the moving pulleys 51 to translationally move toward the first link 21.

At the outer side and the inner side, the other-end-side led out portion of the wire 32 introduced into the joint connection 15 through the tube 45 from each of the elastic structures 31 is wrapped on the outer periphery of the moving pulley 51 accommodated in the joint connection 15 (i.e. the outer periphery of the knee joint mechanism 5 adjacent to the first link 21), as illustrated in FIG. 5.

Further, the other-end-side led out portion of the wire 32 wrapped on the outer periphery of the moving pulley 51 is passed through a hole formed in the partition wall 15a of the outer joint connection 15 via the outer periphery of the outer moving pulley 51 and led into the upper portion of the outer joint connection 15 of the first element frame 12.

Similarly, the other-end-side led out portion of the wire 32 wrapped on the outer periphery of the inner moving pulley 51 is passed through a hole formed in a partition wall 15a of the inner joint connection 15 via the outer periphery of the inner moving pulley 51 and led into the upper portion of the inner joint connection 15 of the second element frame 13.

Further, the other-end-side led out portion of the wire 32 of the first element frame 12 side and the other-end-side led out portion of the wire 32 of the second element frame 13 side are passed through a tube 56 of the first element frame 12 and through a tube 56 of the second element frame 13, respectively, to a chassis 61 of the actuator device 54. These other-end-side led out portions of the wires 32 are led into the chassis 61 through the holes formed in the chassis 61.

In this case, the tube 56 of the first element frame 12 is disposed to extend from the outer joint connection 15 to the base 11 along the direction in which the first element frame 12 extends, and to further pass through the space outside the thigh frame 2 from the base 11 until reaching the chassis 61.

Further, the tube 56 of the second element frame 13 is disposed to extend from the inner joint connection 15 to the base 11 along the direction in which the second element frame 13 extends, and to further pass through the space outside the thigh frame 2 from the base 11 until reaching the chassis 61.

Further, one end of each of the tubes 56 is in contact with or fixed to a predetermined portion of the partition wall 15a of the joint connection 15. The other end of the tube 56 is in contact with or fixed to a predetermined portion of the outer wall of the chassis 61.

Each of the tubes 56 is configured to exhibit relatively low stiffness against a bending load so as to be bendable to a certain degree, and to exhibit relatively high stiffness (i.e. high resistance to expansion and contraction) against a compression load in the direction of the length of the tube 56. The tube 56 may use, for example, tubes having the same configuration as a brake tube of a bicycle, which is a tube comprising of a densely wound metal coil covered with a resin.

Supplementarily, in the present embodiment, both end portions of the outer peripheral part of the moving pulley 51, at which the moving pulley 51 and the wire 32 are in contact, correspond to the first engagement portion and the second management portion in the present invention. Further, the bearings 52 for the moving pulleys 51 correspond to the joint interlock displacement parts in the present invention.

Figure 7:
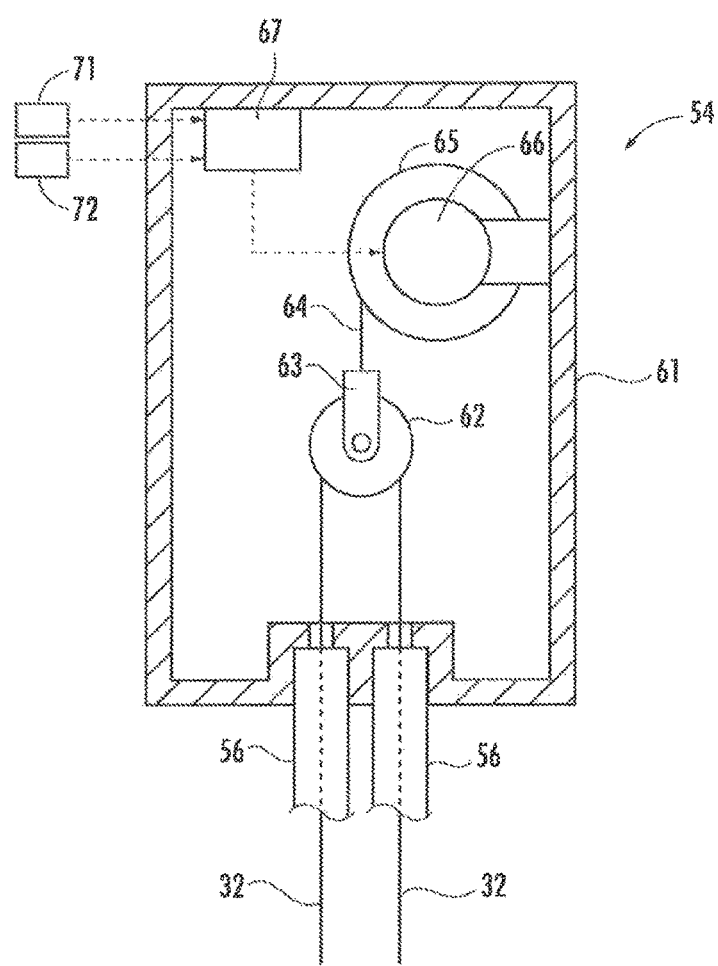
FIG. 7 is a diagram illustrating the configuration of an actuator device provided in the joint power control device illustrated in FIG. 5.

Referring to FIG. 7, in the present embodiment, the other-end-side led out portions of the wires 32 and 32 extending from the outer elastic structure 31 and the inner elastic structure 31, respectively, to the chassis 61 are connected in the chassis 61. In other words, these wires 32 and 32 are comprising of a single wire.

Further, the actuator device 54 has, in the chassis 61, a moving pulley 62 having the wire 32 wound around the outer periphery thereof, a bearing 63 which supports the moving pulley 62 such that the moving pulley 62 is rotatable about its axis of rotation, a pulley 65 connected to the bearing 63 through the intermediary of a wire 64, an electric motor 66 capable of rotatively driving the pulley 65, and a control unit 67 which controls the operation of the electric motor 66. Further, although not illustrated, a power source, such as a battery assembly, for the electric motor 66 and the control unit 67 is also installed in the chassis 61. Alternatively, however, the control unit 67 or the power source may be disposed at a place separate from the chassis 61 of the actuator device 54.

FIG. 7 illustrates only the actuator device 54 for one leg link mechanism 7 attached to either the left leg or the right leg of the person to be assisted P. The chassis 61 may be shared between or separately provided for the actuator device 54 for the leg link mechanism 7 to be attached to the left leg of the person to be assisted P and the actuator device 54 for the leg link mechanism 7 to be attached to the right leg.

The chassis 61 is attached to the person to be assisted P at a place where the chassis 61 does not interfere with the motion of the person to be assisted P. For example, as illustrated FIG. 1 or FIG. 2, the chassis 61 is attached through the intermediary of a belt or the like (not illustrated) to an upper side of the waist on the back of the person to be assisted P such that the chassis 61 moves substantially together with the upper body of the person to be assisted P. Alternatively, the chassis 61 may be attached to, for example, the back of the person to be assisted P or to the upper body on the abdomen side.

The housing of the electric motor 66, i.e. the part to which the stator of the electric motor 66 is fixed, is secured to the chassis 61. Further, the pulley 65 is connected, through the intermediary of a reduction gear (not illustrated) to the output shaft of the electric motor 66 so as to allow an output torque of the electric motor 66 to be transmitted to the pulley 65.

One end of the wire 64 is fixed to the outer periphery of the pulley 65, while the other end of the wire 64 is fixed or locked to the bearing 63 that supports the moving pulley 62.

Further, the moving pulley 62 and the bearing 63 can be translationally moved toward or away from the pulley 65 according to a change in the amount of winding of the wire 64 on the pulley 65. In this case, the wire 32 is wound on the semicircular portion of the outer periphery of the moving pulley 62, which semicircular portion is adjacent to the pulley 65. The direction in which the moving pulley 62 and the bearing 63 move toward the pulley 65 is the direction in which the wire 32 is pulled into the chassis. The direction in which the moving pulley 62 and the bearing 63 move away from the pulley 65 is the direction in which the wire 32 is pulled out of the chassis 61.

Hence, a translational force in the direction for pulling the wire 32 into the chassis 61 is applied to the moving pulley 62 through the intermediary of the wire 64 and the bearing 63 by imparting a torque in the direction for winding the wire 64 onto the pulley 65 from the electric motor 66 to the pulley 65. The translational force causes a tensile force to be applied to the wire 32, thus imparting a tension to the wire 32.

The control unit 67, which controls the operation of the electric motor 66, is comprising of an electric circuit unit that includes a CPU, a RAM, a ROM, an interface circuit and the like. The control unit 67 may alternatively be comprising of a plurality of electronic circuit units capable of mutual communication.

The control unit 67 according to the present embodiment receives the detection signals from a rotation sensor 71 that outputs signals based on the rotational angles of the pulley 65 and a ground contact sensor 72 that outputs signals based on whether the leg link mechanisms 7 attached to the legs of the person to be assisted P are in contact with a ground (i.e. whether a leg or legs of the person to be assisted P to which the leg link mechanisms 7 are attached is or are in a support leg state or a free leg state).

The rotation sensor 71 may be comprising of, for example, a rotary encoder, a potentiometer or the like installed to the pulley 65 or the electric motor 66 or the like. Further, the ground contact sensor 72 may be comprising of, for example, a force sensor or the like installed to the foot frame 4 so as to detect the pressure between the foot frame 4 and the sole of a foot of the person to be assisted P.

Further, the control unit 67 controls the operation of the electric motor 66 by executing a preinstalled program while monitoring the detection signals of the rotation sensor 71 and the ground contact sensor 72.

A description will now be given of the operation of the motion assisting apparatus 1 according to the present embodiment.

With the leg link mechanism 7 attached to each of the legs of the person to be assisted P as illustrated in FIG. 1 or FIG. 2, the control unit 67 is actuated.

For each of the leg link mechanisms 7, the control unit 67 controls the operation of the electric motor 66 as described below according to the detection signals of the rotation sensor 71 and the ground contact sensor 72.

If the detection signal of the ground contact sensor 72 indicates that the leg link mechanism 7 is not in contact with the ground, i.e. if the leg to which the leg link mechanism 7 is attached is a free leg, meaning that the foot frame 4 is moving in the air, then the control unit 67 controls the output torque of the electric motor 66 such that a small torque (e.g. a torque of a predetermined value) that permits the prevention of a slack in the wire 32 is imparted to the pulley 65.

In this case, when the leg link mechanism 7 bends or stretches at the knee joint mechanism 5 as the leg with the leg link mechanism 7 attached thereto bends or stretches, the moving pulley 51 in each of the joint connections 15 is displaced (translationally moved) together with the bearing 52 while rotating at the same time in response to the bending or stretching motion. Further, as the moving pulley 51 and the bearing 52 are displaced, the pulley 65 of the actuator device 54 rotates, causing the other-end-side led out portion of the wire 32 from the outer elastic structure 31 and the other-end-side led out portion of the wire 32 from the inner elastic structure 31 to move with respect to the first element frame 12 and the second element frame 13, respectively.

In the situation in which the pulley 65 of the actuator device 54 rotates as the moving pulley 51 is displaced, a compression load is not substantially applied to the elastic structure 31. Hence, in a state in which the elastic force of the elastic structure 31 is not substantially applied to the knee joint mechanism 5.

Therefore, the person to be assisted P can move the leg in the free leg phase in the same manner as a normal motion manner as if the leg link mechanism 7 were not attached to the leg.

Meanwhile, if the detection signal of the ground contact sensor 72 indicates that the leg link mechanism 7 is in contact with the ground, i.e. if the leg to which the leg link mechanism 7 is attached is in the support leg phase (meaning that the foot frame 4 is in contact with the ground), then the control unit 67 controls the output torque of the electric motor 66 according to a detection signal of the rotation sensor 71 such that the rotational angle of the pulley 65 indicated by the output of the rotation sensor 71 is held at a constant angle, i.e. the pulley 65 is held in the non-rotation state.

When the output torque of the electric motor 66 is controlled as described above, the bearing 63 of the moving pulley 62 in the chassis 61 is locked with respect to the chassis 61. In this condition, as the degree of bending of the crus frame 3 relative to the thigh frame 2 is increased, i.e. as the leg link mechanism 7 is bent at the knee joint mechanism 5 from a stretched state, the moving pulley 51 in each of the joint connections 15 is displaced (translationally moved) in a direction toward the first link 21 of the knee joint mechanism 5.

At this time, as the moving pulley 51 in each of the joint connections 15 is displaced, the other-end-side led out portion of the wire 32 from each of the elastic structures 31 is pulled. This causes the compression load from the wire 32 to be applied to the upper end of the elastic structure 31.

Thus, the elastic structure 31 is compressed. At the same time, the output torque of the electric motor 66 is controlled such that the tension imparted to the wire 32 increases to a tension that balances the elastic force generated by the compression of the elastic structures 31.

Thus, the elastic force of the elastic structure 31 will be imparted as the joint power in the direction for stretching the leg link mechanism 7 to the knee joint mechanism the same side (the outer side or the inner side) as the elastic structure 31. In this case, the amount of compression of the elastic structure 31 and the resultant elastic force increase as the degree of bending between the thigh frame 2 and the crus frame 3 increases.

As described above, the joint power from the elastic force of the elastic structure 31 is imparted to the knee joint mechanism 5 of the leg link mechanism 7 on the support leg side of the person to be assisted P, thus reducing the load on the support leg of the person to be assisted P when, for example, the person to be assisted P walks, stands up or sits down, squats or stands up front a squatting posture. This makes it possible to assist the motion, namely, the motion of moving the legs, of the person to be assisted P or the like having weakened legs.

The motion assisting apparatus 1 according to the present embodiment has, for example, the operation characteristics illustrated by the graph of FIG. 9. The graph of FIG. 9 illustrates an example of the relationship between the assist force acting on the person to be assisted P by the elastic force of the elastic structure 31 imparted to each of the knee joint mechanisms 5 (i.e. the translational force acting upward with respect to the upper body) and the degree of bending (i.e. the bending angle) between the thigh frame 2 and the crus frame 3.

In this example, the upward translational force from the elastic force of the elastic structure 31 increases with high sensitivity as the degree of bending (the bending degree) between the thigh frame 2 and the crus frame 3 increases in the range in which the degree of bending is relatively small, i.e. the range in which the leg link mechanism 7 is almost fully extended. Further, when the bending degree increases to a certain level, the upward translational force from the elastic force of the elastic structure 31 increases relatively gradually as the bending degree increases.

The operation characteristics of the motion assisting apparatus 1 are not limited to the characteristics illustrated in FIG. 9, and a variety of operation characteristics can be implemented by, for example, the selection of the elastic characteristic of the elastic member of each of the elastic structures 31 or the setting of the shape of the outer peripheral portion of the first link 21 (the portion engaging with the wire 32) in each of the knee joint mechanisms 5.

The motion assisting apparatus 1 according to the present embodiment configured as described above is capable of providing the following advantages.

The elastic member 41 of each of the elastic structures 31 is constructed to have many hermetically sealed air chambers, as in, for example, a closed-cell (closed-pore) rubber sponge. This allows the elastic structures 31 to be lightweight.

Further, each of the elastic members 41 generates, in addition to the elastic force generated by the material thereof, an elastic force generated by the compression (i.e. the reduction in volume) of the plurality of the air chambers in the elastic member 41 (more specifically, the elastic force generated by an increase in the air pressure in the air chambers caused by a reduction in the volume of the air chambers). This enables the elastic structures 31 to increase the elastic forces with high sensitivity by the compression in the direction of the axial center thereof. Hence, the elastic structures 31 are capable of generating relatively large elastic forces even when they are small-sized.

Further, according to the present embodiment, the elastic structure 31 is formed to have the multilayer structure comprising of a plurality of elastic members 41 and the partition plates 42. Further, the wire 32 to which a tension is imparted is inserted in the through hole 43 of the elastic structure 31. This arrangement prevents the occurrence of an abnormal bending state in which the entire elastic structure 31 is excessively bent or the bending direction differs at each local spot in the stacking direction of the elastic structure 31 when the elastic structure 31 is compressed.

Further, according to the present embodiment, the minimum value of the cross-sectional area of the through hole of each of the partition plates 42 of the elastic structure 31 is smaller than the minimum value of the cross-sectional area of the through hole of each of the elastic members 41. This prevents or suppresses the wire 32 from coming in slide contact with the inner peripheral surface of the through hole of each of the elastic members 41 even if the elastic structure 31 is installed to the thigh frame 2 in a bent state, causing the wire 32 to deviate from the center of the through hole 43 of the elastic structure 31, or if the wire 32 deviates from the center of the through hole 43 when the elastic structure 31 is compressed or is expanded from a compressed state. As a result, it is possible to prevent or suppress the occurrence of the friction between the inner peripheral surface of the through hole of the elastic member 41 and the wire 32.

In addition, the inner peripheral surface of the through hole of the partition plate 42 is curved as described above. Further, the inner peripheral surface is formed of a slide material. Hence, even if the wire 32 comes in slide contact with the inner peripheral surface of the through hole of the partition plate 42, the force of the friction between the wire 32 and the partition plate 42 is minimized.

Further, the elastic member 41 and the partition plate 42 that are stacked are fixed to each other at their contact surfaces. Therefore, no friction between the contact surfaces will occur when the elastic structure 31 is compressed or expanded from a compressed state.

This arrangement permits maximized prevention of the elastic energy or the like accumulated by the compression of the elastic structure 31 from being wasted as heat energy attributable to the friction. This in turn permits a reduced energy loss. Further, the elastic energy accumulated at the elastic structure 31 can be efficiently converted into the joint power to be applied to the knee joint mechanism 5.

Further, the portion adjacent to the inner periphery around the through hole in the partition plate 42 is formed to be the thick portion 42a. In addition, the inner peripheral surface of the through hole on the inner side of the thick portion 42a is curved as described above. Hence, even if the wire 32 comes in contact with the inner peripheral surface of the through hole of the partition plate 42 when the elastic structure 31 is compressed or is expanded from the compressed state, the contact pressure is dispersed in the direction of the length of the through hole of the partition plate 42. This prevents the pressure of contact between the wire 32 and the partition plate 42 from being concentrated on a local spot of the wire 32 or the partition plate 42. As a result, the occurrence of breakage, damage or the like of the wire 32 can be prevented, thus permitting enhanced durability of the wire 32 and the like.

Further, according to the present embodiment, the base frame of each of the thigh frames 2 is comprising of the first element frame 12, which extends from the base 11 disposed on one side of the waist of the person to be assisted P to the outer side of a knee along the outer side of the thigh of the person to be assisted P, and the second element frame 13, which extends from the base 11 obliquely on the front side of the thigh to the inner side of the knee.

Therefore, no frame exists on the inner sides of places adjacent to the bases of the legs of the person to be assisted P. This makes it possible to prevent the thigh frame 2 of the leg link mechanism 7 for the right leg of the person to be assisted P and the thigh frame 2 of the leg link mechanism 7 for the left leg from interfering with each other on the inner sides of the thighs of the both legs.

Further, the first element frame 12 of the thigh frame 2 extends substantially in the vertical direction, and the second element frame 13 extends obliquely downward from the base 11. This arrangement allows the thigh frame 2 to exhibit relatively high bending stiffness in the pitch direction. Thus, it is possible to effectively apply, to the person to be assisted P, the force for pushing up the upper body of the person to be assisted P through the intermediary of the body support member 14 when the person to be assisted P bends his or her leg.

Further, the first element frame 12 and the second element frame 13 of the thigh frame 2 can be bent relatively easily to change the interval between their lower portions. This arrangement allows the thigh frame 2 to fit a wide range of thickness of thighs. In addition, maximized prevention of the person to be assisted P from feeling restrained can be achieved.

Further, the second element frame 13 of the thigh frame 2 extends obliquely downward from the outer side to the inner side of a thigh on the front side of the thigh. In addition, the second element frame 13 smoothly curves.

This arrangement enables the person to be assisted P to easily grasp each portion of the second element frame 13 from the upper end thereof to the lower end thereof while taking a natural posture of his or her arm or the like when, for example, the person to be assisted P is sitting on a chair or the like. The arrangement also enables the person to be assisted P to effortlessly exert a force on the second element frame 13 while grasping a portion of the second element frame 13. This enables the person to be assisted P to easily attach or detach the leg link mechanism 7.

Further, the body support member 14 of the thigh frame 2 extends obliquely, on the back side of the thigh, from the base 11 to the lower end portion of the second element frame 13. This arrangement makes it possible to support the thigh from the back side by the body support member 14 from the place on the bottom side to the place on the top side of the thigh when a leg (a support leg) of the person to be assisted P is being bent, i.e. when the elastic force is being applied by the elastic structure 31 to the knee joint mechanism 5.

In particular, the base 11 is a portion disposed at a level that is higher than the inner root of a leg of the person to be assisted P. Therefore, not only the thigh of the person to be assisted P but also a portion in the vicinity of a hip joint or a portion in the vicinity of the ischium can be supported by the body support member 14 extending from the base 11.

Thus, the translational force in the direction for pushing up the upper body of the person to be assisted P can be effectively applied to the person to be assisted P while preventing the translational force from being concentrated on any local spot of the person to be assisted P.

Further, the base 11, which is the upper end portion of the thigh frame 2, is disposed at the level that is higher than the root on the inner side of a leg of the person to be assisted P and disposed at a level that is lower than the hipbone of the person to be assisted P. This makes it possible to prevent the upper end portion of the thigh frame 2 from being pressed against the buttocks of the person to be assisted P when the person to be assisted P turns his or her leg outward or to prevent the upper end portion of the thigh frame 2 from coming in contact with the side face of the upper body of the person to be assisted P when the person to be assisted P bends his or her upper body sideways.

Further, according to the present embodiment, the joint power control device 8 imparts the elastic force generated by the elastic structure 31 to the knee joint mechanism 5 through the intermediary of the first link 21 of the knee joint mechanism 5. In this case, each of the knee joint mechanisms 5 is configured as described above, so that the rotational displacement amount of the first link 21 can be controlled to be relatively small even when the person to be assisted P bends his or her stretched leg to a maximum degree, as seen from FIG. 4.

Hence, the required expansion and contraction amount of each of the elastic structures 31 can be controlled to a relatively small amount, so that the space required for disposing each of the elastic structures 31 can be reduced. This permits a higher degree of freedom of the disposition of the elastic structures 31 and a reduced size of the joint power control device 8.

Further, as described above, when the person to be assisted P bends or stretches his or her leg, the relative displacements of the thigh frame 2 and the crus frame 3 corresponding to the thigh and the crus, respectively, of the leg hardly take place, thus hardly requiring an allowance space for the relative displacements. Hence, the joint power control device 8 can be made smaller.

Further, in the joint power control device 8 in the present embodiment, the joint power is imparted to the first link 21 of the knee joint mechanism 5 through the intermediary of the moving pulley 51. In this case, the resultant force of the elastic force of the elastic structure 31 and the tension imparted to the wire 32 (a force of a magnitude that is approximately double that of the elastic force) is imparted to the first link 21 of the knee joint mechanism 5 through the intermediary of the bearing 52 of the moving pulley 51 and the wire 55.

Hence, the compact elastic structure 31 can be used to impart relatively large joint power to the knee joint mechanism 5.

Further, the joint power control device 8 in the present embodiment is adapted to transmit the elastic force of the elastic structure 31 to the knee joint mechanism 5 through the intermediary of the moving pulley 51. This allows the elastic structure 31 to expand or contract at a fixed mounting place of the thigh frame 2. Hence, the space required for installing the elastic structure 31 is reduced. This in turn permits a reduced size of the portion (the thigh frame 2) where the elastic structure 31 is installed.

[Modifications]

The embodiments of the present invention are not limited to the embodiments described above, and may adopt a variety of modes. The following will describe some modifications.

In the embodiments described above, the elastic members 41 of the elastic structures 31, which have been illustrated, have the cylindrical shape. Alternatively, however, the elastic members 41 of the elastic structures 31 are not limited to the cylindrical shape and may adopt a variety of shapes.

Further, a guide tube extending in the stacking direction of the elastic structure 31 may be externally inserted onto the elastic structure 31 so as to cause the elastic structure 31 to be compressed along the inner peripheral surface of the guide tube.

Figure 10:
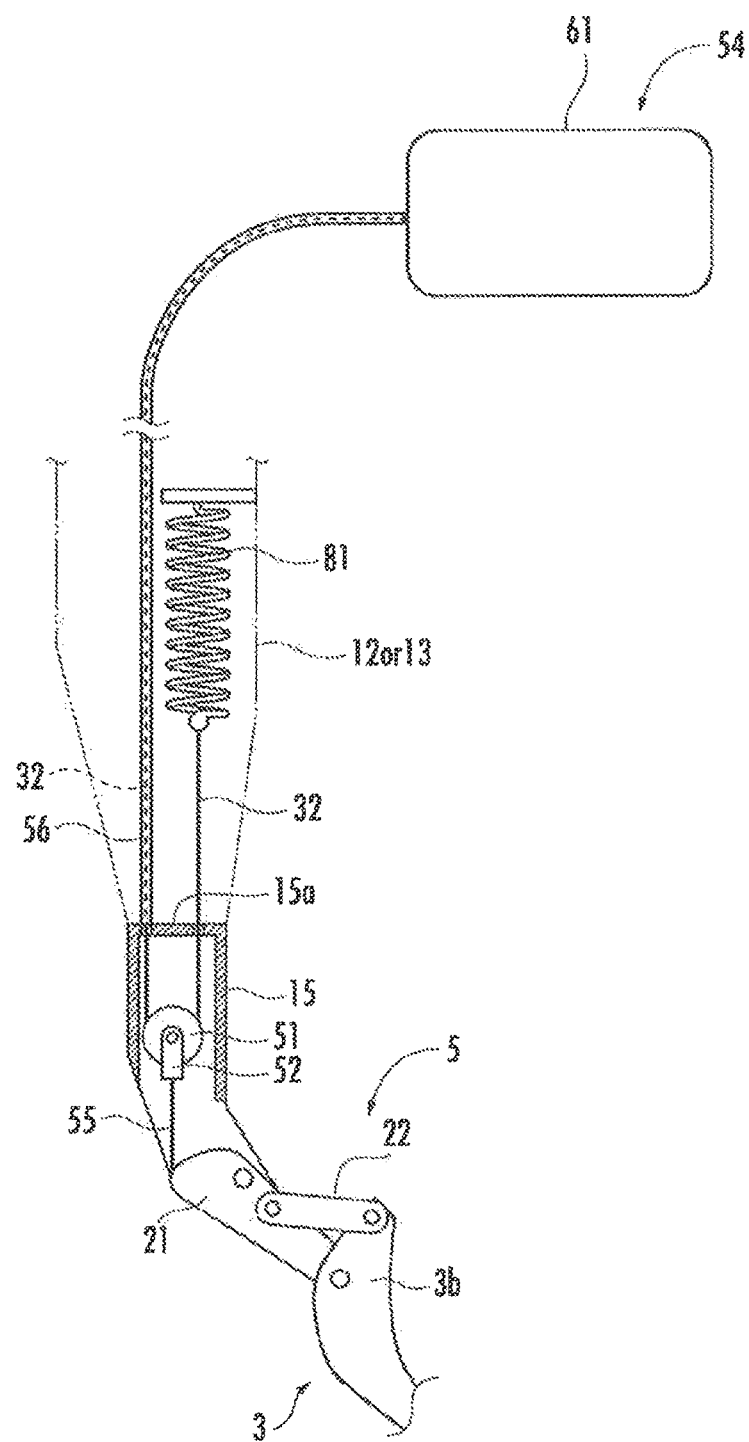
FIG. 10 is a diagram illustrating a configuration in a modification of a first example of the joint power control device.

Further, in place of the elastic structures 31, regular elastic members, such as coil springs, may be used. In this case, a configuration illustrated in, for example, FIG. 10 may be adopted. In this example, inside a first element frame 12 or a second element frame 13, the upper end of a coil spring 81 is fixed or locked to the first element frame 12 or the second element frame 13. Further, a wire 32 (flexible lengthy member) connected to the lower end of the coil spring 81 is wrapped on a moving pulley 51 in a joint connection 15.

Further, the embodiments described above have used the wire 32 as the flexible lengthy member. Alternatively, however, the flexible lengthy member may be belt-shaped or chain-shaped.

Further, the joint power control device 8 may adopt a variety of modes rather than being limited to the configurations described above.

For example, the joint power control device 8 may be configured to impart the joint power to only one of the outer knee joint mechanism 5 and the inner knee joint mechanism 5.

Figure 11:
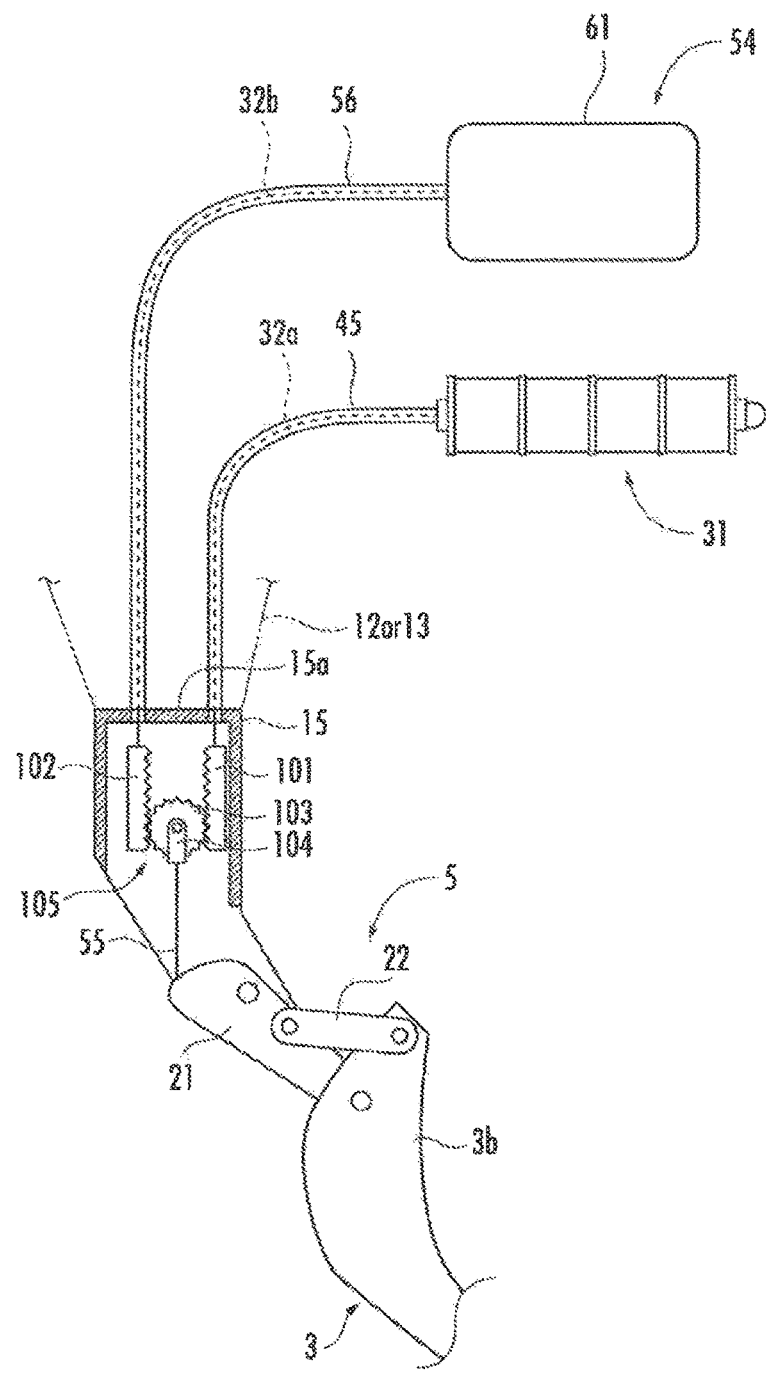
FIG. 11 is a diagram illustrating a configuration in a modification of a second example of the joint power control device.

Further, in place of the power transmission movable mechanism 53 having the moving pulley 51 and the bearing 52, a power transmission movable mechanism configured using a differential mechanism may be used. For example, a power transmission movable mechanism 105 having a first rack 101, a second rack 102, a gear 103, and a bearing 104 that supports the gear 103 such that the gear 103 is rotatable about its axis of rotation, as illustrated FIG. 11.

In this example, the power transmission movable mechanism 105 is installed inside the joint connections 15 of the thigh frame 2. The first rack 101 and the second rack 102 are disposed, facing against each other. Further, the first rack 101 and the second rack 102 are provided such that they are slidable in the same direction along rails (not illustrated). The movable ranges of the first rack 101 and the second rack 102 are restricted by stoppers or the like (not illustrated).

Further, the gear 103 is disposed between the racks 101 and 102 and engaged with the racks 101 and 102.

Further, an end of a wire 32a introduced into the joint connection 15 from an elastic structure 31 through a tube 45 is connected to the first rack 101. An end of the wire 32a on the opposite side from the first rack 101 is locked to one end (the right end in FIG. 11) of the elastic structure 31, as with the foregoing embodiments.

Further, an end of a wire 32b that extends from the inside of the joint connection 15 through a tube 56 into a chassis 61 of an actuator device 54 is connected to the second rack 102. As with the foregoing embodiments, the wire 32b is wrapped on a moving pulley 62 in the chassis 61 of the actuator device 54. The wires 32a and 32b are separated.

The bearing 104 of the gear 103 is connected to the outer periphery of the first link 21 of the knee joint mechanism 5 through the intermediary of a wire 55, as with the bearing 52 of the moving pulley 51 in the foregoing embodiments.

Supplementarily, in this example, the first rack 101 and the second rack 102 correspond to the first engagement part and a second engagement part, respectively, in the present invention. Further, the bearing 104 of the gear 103 corresponds to the joint interlock displacement part in the present invention.

Even in the case where the power transmission movable mechanism 105 configured as described above is used, the joint power can be imparted to each of the knee joint mechanisms 5 in the state, in which a leg of the person to be assisted P is in contact with a ground, by controlling an electric motor 66 of the actuator device 54 in the same manner as that in the foregoing embodiments.

In this case, in a state wherein the electric motor 66 generates a small output torque for removing a slack from the wire 32a, bending or stretching the leg link mechanism 7 causes the second rack 102 to slide and the gear 103 and the bearing 104 to translationally move at the same time.

Further, if the electric motor 66 is controlled to maintain the pulley 65 in the non-rotation state, bending or stretching the leg link mechanism 7 causes the first rack 101 to slide and the gear 103 and the bearing 104 to translationally move at the same time.

Further, in the foregoing embodiments or modifications, the outer periphery of the first link 21 of each of the knee joint mechanisms 5 is shaped like a pulley, and the flexible wire 55 is connected to the outer periphery. However, the mechanism that transmits power to the first link 21 may be a different mechanism.

Figure 12A:
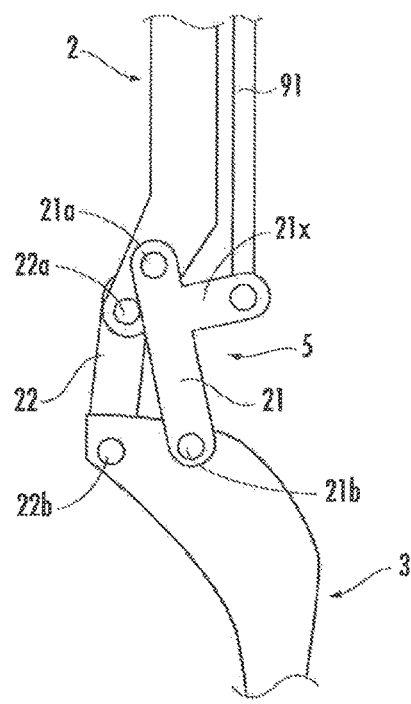
FIG. 12A and FIG. 12B are diagrams illustrating other examples of the connection structure between a knee joint mechanism and a lengthy member.

As illustrated in, for example, FIG. 12A, an arm 21x may be formed on the first link 21, and the power, i.e. the translational force, may be imparted to the first link 21 through the intermediary of a rod 91 journaled on the arm 21x. In this case, the end of the rod 91 on the opposite side from the arm 21x may be connected to, for example, the bearing 52 of the moving pulley 51 or the bearing 104 of the gear 103. In this example, the connection between the arm 21x and the rod 91 corresponds to the outer periphery of the first link in the present invention. Further, the rod 91 corresponds to the lengthy member in the present invention.

Figure 12B:
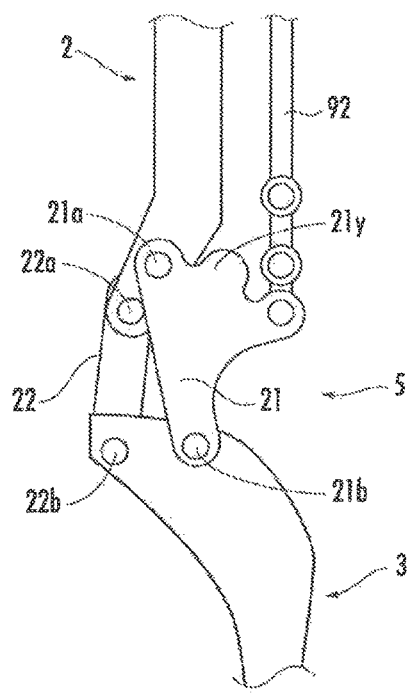

Alternatively, as illustrated in FIG. 12B, a sprocket 21y may be formed on the outer periphery of the first link 21, and the power, i.e. the translational force, may be imparted to the first link 21 through the intermediary of a chain 92 engaged with the sprocket 21y. In this case, the end of the chain 92 on the opposite side from the sprocket 21y may be connected to, for example, the bearing 52 of the moving pulley 51 or the bearing 104 of the gear 103. In this example, the sprocket 21y corresponds to the outer periphery of the first link in the present invention. Further, the chain 92 corresponds to the lengthy member in the present invention.

Further, the foregoing embodiments have illustrated the power transmission movable mechanism 53 and the elastic structure 31 installed to the thigh frame 2. Alternatively, however, the power transmission movable mechanism 53 and the elastic structure 31 may be installed to a place other than the thigh frame 2.

For example, the power transmission movable mechanism 53 and the elastic structure 31 may be installed in a chassis 61 of an actuator device 54, as illustrated in FIG. 13. In this example, an end (the left end in FIG. 13) of the elastic structure 31 is fixed to the chassis 61. In FIG. 13, the power transmission movable mechanism 53 has a moving pulley 51. Alternatively, however, the power transmission movable mechanism 53 may be replaced by the power transmission movable mechanism 105 having the racks 101, 102 or the like.

Further, in the foregoing embodiments, the joint power in the direction in which the leg link mechanism 7 is stretched has been applied to each of the knee joint mechanisms 5. Alternatively, however, the joint power control device may be configured to apply the joint power in the bending direction to the knee joint mechanism 5.

Further, the actuator device 54 is not limited to that in the foregoing embodiments. For example, the actuator device 54 may be provided with a brake unit, which is capable of switching between a mode for braking or locking the pulley 65 to be unrotatable and a mode for releasing the braking or locking mode, in place of the electric motor 66. Further, a clutch mechanism capable of cutting off the power transmission between the electric motor 66 and the pulley 65 may be interposed therebetween. In addition, a pretension mechanism which imparts a low tension to the wires 32 or 32a, 32b may be provided separately from the electric motor 66 or the brake unit in order to prevent the wires 32 or 32a, 32b from slacking.

Further, the leg link mechanisms 7 of the motion assisting apparatus 1 are not limited to the constructions described above. For example, the knee joint mechanism of each of the leg link mechanisms 7 may be comprising of a single-axis joint mechanism having a degree of freedom of rotation about one axis in, for example, the direction of the pitch axis.

Further, for example, the thigh frame 2, the crus frame 3 and the foot frame 4 may have constructions that are different from those in the foregoing embodiments.

Further, each of the leg link mechanism may be configured, for example, to have the knee joint mechanism only on one of the outer side and the inner side of the knee.

Further, for example, the ankle joint mechanism 6 and the foot frame 4 of the leg link mechanism 7 may be omitted. In addition, the leg link mechanism may be configured such that the lower end portion of the crus frame 3 is bound through a belt or the like to the ankle of a leg.

Further, the ankle joint mechanism 6 may be comprising of, for example, a free joint or the like.

Further, the base 11 of the thigh frame 2 may be disposed on the outer side of an upper portion of the thigh.

Further, the leg link mechanisms may adopt, for example, the structure illustrated in FIG. 14 and FIG. 15.

In this example, a leg link mechanism 7A for each leg of the person to be assisted P differs from that in the foregoing embodiments only in the construction of a thigh frame 120. In this case, the thigh frame 120 has a base 121, which is disposed at an upper level of each leg, and more specifically, at a place on the front of the waist of the person to be assisted P that is adjacent to the side surface (namely, a place located approximately at 45 degrees with respect to the longitudinal direction and the lateral direction), and a first element frame 122 and a second element frame 123, which are bifurcated and extended downward from the base 121.

The first element frame 122 extends obliquely downward from the base 121 toward the outer knee joint mechanism 5 on the front side of the thigh of on a leg of the person to be assisted P. Further, the lower end portion of the first element frame 122 (corresponding to the joint connection 15) is connected to the outer knee joint mechanism 5.

Further, the second element frame 123 extends obliquely downward from the base 121 toward the inner knee joint mechanism 5 on the front side of the thigh of the leg of the person to be assisted P. Further, the lower end portion of the second element frame 123 (corresponding to the joint connection 15) is connected to the inner knee joint mechanism 5.

Further, the thigh frame 120 has a body support member 124 disposed on the rear side of the thigh of the leg of the person to be assisted P. The body support member 124 is extended between the base 11 and the lower end portion of the second element frame 123 such that the body support member 124 extends from the base 11 to the lower end portion of the second element frame 123 via the back of the buttock of the person to be assisted P.

The structure of the leg link mechanism 7A illustrated in FIG. 14 and FIG. 15 is the same as that of the leg link mechanism 7 in the foregoing embodiments except for the aspect described above.

The thigh frame 120 in the leg link mechanism 7A configured as described above also exhibits high bending stiffness in the pitch direction. Further, an assisting force in the direction for pushing up the upper body of the person to be assisted P can be properly applied to the person to be assisted P through the intermediary of the body support member 124 by imparting the joint power to the knee joint mechanisms 5 in the same manner as that in the foregoing embodiments.

As described above, the base 121 is disposed at a place located in the direction of approximately 45 degrees with respect to the longitudinal direction and the lateral direction of the person to be assisted P. This prevents the base 121 from coming in contact with the abdomen of the person to be assisted P when the person to be assisted P squats or the like.

What is claimed is:

1. A joint mechanism control device including a joint mechanism connecting a first member and a second member in a relatively displaceable manner, and a joint power control device adapted to control a joint power which is a power applied to the joint mechanism, comprising:

a power transmission movable mechanism having a joint interlock displacement part connected to the joint mechanism such that the joint interlock displacement part is displaced according to a change in an amount of relative displacement of the first member and the second member caused by a motion of the joint mechanism, and a first engagement part and a second engagement part, which are engaged with a first flexible lengthy member and a second flexible lengthy member such that the first engagement part and the second engagement part are displaced as the first flexible lengthy member and the second flexible lengthy member move, the power transmission movable mechanism being configured such that the joint interlock displacement part is displaced by a displacement amount specified based on an amount of displacement of the first engagement part and the second engagement part, and a resultant force comprising of a force applied from the first flexible lengthy member and a force applied from the second flexible lengthy member to the first engagement part and the second engagement part, respectively, and a force applied from the joint mechanism to the joint interlock displacement part are balanced;

a control mechanism connected to an end of the first flexible lengthy member on an opposite side from the first engagement part, enabling the control mechanism to control the movement of the first flexible lengthy member; and an elastic structure engaged with the second flexible lengthy member such that the elastic structure generates an elastic force as the second flexible lengthy member moves, wherein the power transmission movable mechanism includes: a first rack and a second rack, which are disposed facing against each other and provided to be slidable in a same direction; a gear which is disposed between the first rack and the second rack and engaged with the first rack and the second rack; and a bearing which supports the gear such that the gear is rotatable about its axis of rotation, the first rack and the second rack serving as the first engagement part and the second engagement part, respectively, and the bearing serving as the joint interlock displacement part.

2. The joint mechanism control device according to claim 1, wherein the power transmission movable mechanism includes: a moving pulley, a single flexible lengthy member wound on an outer periphery of the moving pulley, said single flexible lengthy member being composed by connecting the first flexible lengthy member and the second flexible lengthy member into one flexible lengthy member.

3. The joint mechanism control device according to claim 1, wherein the elastic structure is configured to have a first end to which an end of the second flexible lengthy member on an opposite side from the second engagement part is locked, and a second end provided to maintain a constant distance from a middle portion of a disposition path of the second flexible lengthy member along the disposition path, and to generate an elastic force according to elastic deformation between the first end and the second end.

4. The joint mechanism control device according to claim 1,
wherein the elastic structure is configured to have a first end to which an end of the second flexible lengthy member on an opposite side from the second engagement part is locked, and a second end provided to maintain a constant distance from a middle portion of a disposition path of the second flexible lengthy member along the disposition path, and to generate an elastic force according to elastic deformation between the first end and the second end; and
wherein the elastic structure is formed to have a multilayer structure composed by alternately stacking a plurality of elastic members, each of which includes one or more hermetically sealed air chambers, and a plurality of partition plates having stiffness that is higher than stiffness of the elastic members, a through hole being formed to extend in a direction of the stacking, and a total length in the direction of the stacking being larger than a minimum width of each of the elastic members in a direction orthogonal to the direction of the stacking,
one end of both ends of the elastic structure in the direction of the stacking and the other end thereof are defined as the first end and the second end, respectively,
the end of the second flexible lengthy member on the opposite side from the second engagement part is inserted in the through hole from the second end of the elastic structure and locked to the first end of the elastic structure, and
volume of each of the air chambers decreases by compression of respective each of said elastic members.

5. The joint mechanism control device according to claim 1,
wherein the first member and the second member are members adapted to be attached to a person such that the members move integrally with a thigh and a crus, respectively, of a leg of the person.

6. The joint mechanism control device according to claim 5,
wherein the first member and the second member are comprising of frames adapted to be attached to the person such that the frames move integrally with the thigh and the crus, respectively, of the leg of the person, and the elastic structure and the power transmission movable mechanism are installed to the frame constituting the first member, and
the control mechanism is adapted to be attached to an upper body of the person.

7. The joint mechanism control device according to claim 5,
wherein the joint mechanism includes a first link connected to the first member and the second member through an intermediary of a first joint shaft and a second joint shaft, respectively, in a pitch axis direction such that the first link is relatively rotatable in a pitch direction with respect to the first member and the second member, respectively, and a second link connected to the first member and the second member through an intermediary of a third joint shaft and a fourth joint shaft, respectively, in the pitch axis direction such that the second link is relatively rotatable in the pitch direction with respect to the first member and the second member, respectively,
the first, second, third and fourth joint shafts are disposed such that
(a) the second joint shaft is positioned at a front side of the fourth joint shaft, and (b) an interval between the first joint shaft and the second joint shaft is denoted by D1, an interval between the third joint shaft and the fourth joint shaft is denoted by D2, an interval between the first joint shaft and the third joint shaft is denoted by Da, and an interval between the second joint shaft and the fourth joint shaft is denoted by Db, so that a relationship expressed by D1>Da and D1+Db>D2+Da holds.

8. The joint mechanism control device according to claim 7,
wherein the joint interlock displacement part of the power transmission movable mechanism is connected through an intermediary of a lengthy member to an outer periphery of a portion of the first link that is adjacent to the first joint shaft.

9. A joint mechanism control device including a joint mechanism connecting a first member and a second member in a relatively displaceable manner, and a joint power control device adapted to control a joint power which is a power applied to the joint mechanism, comprising:
a power transmission movable mechanism having a joint interlock displacement part connected to the joint mechanism such that the joint interlock displacement part is displaced according to a change in an amount of relative displacement of the first member and the second member caused by a motion of the joint mechanism, and a first engagement part and a second engagement part, which are engaged with a first flexible lengthy member and a second flexible lengthy member such that the first engagement part and the second engagement part are displaced as the first flexible lengthy member and the second flexible lengthy member move, the power transmission movable mechanism being configured such that the joint interlock displacement part is displaced by a displacement amount specified based on an amount of displacement of the first engagement part and the second engagement part, and a resultant force comprising of a force applied from the first flexible lengthy member and a force applied from the second flexible lengthy member to the first engagement part and the second engagement part, respectively, and a force applied from the joint mechanism to the joint interlock displacement part are balanced;

a control mechanism connected to an end of the first flexible lengthy member on an opposite side from the first engagement part, enabling the control mechanism to control the movement of the first flexible lengthy member; and an elastic structure engaged with the second flexible lengthy member such that the elastic structure generates an elastic force as the second flexible lengthy member moves, wherein the control mechanism is configured to be capable of operating in at least a mode for preventing the first flexible lengthy member from moving and a mode for clearing the mode for the prevention.

10. The joint mechanism control device according to claim 9,
wherein the first member and the second member are members adapted to be attached to a person such that the members move integrally with a thigh and a crus, respectively, of a leg of the person.

11. The joint mechanism control device according to claim 10,
wherein the first member and the second member are comprising of frames adapted to be attached to the person such that the frames move integrally with the thigh and the crus, respectively, of the leg of the person, and the elastic structure and the power transmission movable mechanism are installed to the frame constituting the first member, and the control mechanism is adapted to be attached to an upper body of the person.

12. The joint mechanism control device according to claim 10,
wherein the joint mechanism includes a first link connected to the first member and the second member through an intermediary of a first joint shaft and a second joint shaft, respectively, in a pitch axis direction such that the first link is relatively rotatable in a pitch direction with respect to the first member and the second member, respectively, and a second link connected to the first member and the second member through an intermediary of a third joint shaft and a fourth joint shaft, respectively, in the pitch axis direction such that the second link is relatively rotatable in the pitch direction with respect to the first member and the second member, respectively, the first, second, third and fourth joint shafts are disposed such that (a) the second joint shaft is positioned at a front side of the fourth joint shaft, and (b) an interval between the first joint shaft and the second joint shaft is denoted by D1, an interval between the third joint shaft and the fourth joint shaft is denoted by D2, an interval between the first joint shaft and the third joint shaft is denoted by Da, and an interval between the second joint shaft and the fourth joint shaft is denoted by Db, so that a relationship expressed by D1>Da and D1+Db>D2+Da holds.

13. The joint mechanism control device according to claim 12,
wherein the joint interlock displacement part of the power transmission movable mechanism is connected through an intermediary of a lengthy member to an outer periphery of a portion of the first link that is adjacent to the first joint shaft.

14. A joint mechanism control device including a joint mechanism connecting a first member and a second member in a relatively displaceable manner, and a joint power control device adapted to control a joint power which is a power applied to the joint mechanism, comprising:

a power transmission movable mechanism having a joint interlock displacement part connected to the joint mechanism such that the joint interlock displacement part is displaced according to a change in an amount of relative displacement of the first member and the second member caused by a motion of the joint mechanism, and a first engagement part and a second engagement part, which are engaged with a first flexible lengthy member and a second flexible lengthy member such that the first engagement part and the second engagement part are displaced as the first flexible lengthy member and the second flexible lengthy member move, the power transmission movable mechanism being configured such that the joint interlock displacement part is displaced by a displacement amount specified based on an amount of displacement of the first engagement part and the second engagement part, and a resultant force comprising of a force applied from the first flexible lengthy member and a force applied from the second flexible lengthy member to the first engagement part and the second engagement part, respectively, and a force applied from the joint mechanism to the joint interlock displacement part are balanced;

a control mechanism connected to an end of the first flexible lengthy member on an opposite side from the first engagement part, enabling the control mechanism to control the movement of the first flexible lengthy member; and an elastic structure engaged with the second flexible lengthy member such that the elastic structure generates an elastic force as the second flexible lengthy member moves, wherein the elastic structure is formed to have a multilayer structure composed by alternately stacking a plurality of elastic members, each of which includes one or more hermetically sealed air chambers, and a plurality of partition plates having stiffness that is higher than that of the elastic members, a through hole being formed to extend in a direction of the stacking, and a total length in the direction of the stacking being larger than a minimum width of each of the elastic members in a direction orthogonal to the direction of the stacking, the second flexible lengthy member is inserted in the through hole of the elastic structure, and volume of each of the air chambers decreases by compression of respective each of said elastic members.

15. The joint mechanism control device according to claim 14,
wherein the first member and the second member are members adapted to be attached to a person such that the members move integrally with a thigh and a crus, respectively, of a leg of the person.

16. The joint mechanism control device according to claim 15,
wherein the first member and the second member are comprising of frames adapted to be attached to the person such that the frames move integrally with the thigh and the crus, respectively, of the leg of the person, and the elastic structure and the power transmission movable mechanism are installed to the frame constituting the first member, and the control mechanism is adapted to be attached to an upper body of the person.

17. The joint mechanism control device according to claim 15,
wherein the joint mechanism includes a first link connected to the first member and the second member through an intermediary of a first joint shaft and a second joint shaft, respectively, in a pitch axis direction such that the first link is relatively rotatable in a pitch direction with respect to the first member and the second member, respectively, and a second link connected to the first member and the second member through an intermediary of a third joint shaft and a fourth joint shaft, respectively, in the pitch axis direction such that the second link is relatively rotatable in the pitch direction with respect to the first member and the second member, respectively, the first, second, third and fourth joint shafts are disposed such that (a) the second joint shaft is positioned at a front side of the fourth joint shaft, and (b) an interval between the first joint shaft and the second joint shaft is denoted by D1, an interval between the third joint shaft and the fourth joint shaft is denoted by D2, an interval between the first joint shaft and the third joint shaft is denoted by Da, and an interval between the second joint shaft and the fourth joint shaft is denoted by Db, so that a relationship expressed by D1>Da and D1+Db>D2+Da holds.

18. The joint mechanism control device according to claim 17,
wherein the joint interlock displacement part of the power transmission movable mechanism is connected through an intermediary of a lengthy member to an outer periphery of a portion of the first link that is adjacent to the first joint shaft.

\* \* \* \* \*